(12) United States Patent
Koelling et al.

(10) Patent No.: US 8,170,705 B2
(45) Date of Patent: May 1, 2012

(54) INTERACTIVE ON-DEMAND ORTHOTIC VENDING MACHINE AND METHOD OF PRODUCING ORTHOTIC INCLUDING DISC VERSION

(75) Inventors: Fred Koelling, Foster City, CA (US); Venugopal Subramanyam, Fremont, CA (US)

(73) Assignee: Alipes, Inc., Ladera Ranch, CA (US)

( * ) Notice: Subject to any disclaimer, the term of this patent is extended or adjusted under 35 U.S.C. 154(b) by 869 days.

(21) Appl. No.: 11/506,979

(22) Filed: Aug. 17, 2006

(65) Prior Publication Data

US 2007/0055405 A1  Mar. 8, 2007

Related U.S. Application Data

(60) Provisional application No. 60/709,878, filed on Aug. 19, 2005, provisional application No. 60/793,446, filed on Apr. 20, 2006.

(51) Int. Cl.
*G06F 19/00* (2011.01)
*G01B 5/00* (2006.01)

(52) U.S. Cl. .......................................... 700/117; 702/33

(58) Field of Classification Search ................... 700/117; 702/33
See application file for complete search history.

(56) References Cited

U.S. PATENT DOCUMENTS

| | | | |
|---|---|---|---|
| 4,449,264 A | 5/1984 | Schwartz | |
| 4,454,618 A | 6/1984 | Curchod | |
| 4,510,636 A | 4/1985 | Phillips | |
| 4,517,696 A | 5/1985 | Schartz | |
| 4,876,758 A * | 10/1989 | Rolloff et al. | 12/142 N |
| 5,088,503 A | 2/1992 | Seitz | |
| 5,336,459 A | 8/1994 | Barna | |
| 5,449,256 A | 9/1995 | Sundman | |
| 5,640,779 A | 6/1997 | Rolloff | |
| 5,689,446 A | 11/1997 | Sundman | |
| 5,941,835 A * | 8/1999 | Sundman | 600/592 |
| 6,205,230 B1 | 3/2001 | Sundman | |
| 6,331,893 B1 * | 12/2001 | Brown et al. | 356/601 |
| 6,430,831 B1 | 8/2002 | Sundman | |
| 6,493,958 B1 | 12/2002 | Tadin | |
| 6,625,897 B2 | 9/2003 | Tadin | |
| 6,804,571 B2 * | 10/2004 | Fullen et al. | 700/118 |
| 6,864,687 B2 | 3/2005 | Walker | |
| 6,904,692 B2 | 6/2005 | Tadin | |
| 7,019,529 B2 | 3/2006 | Walker | |
| 7,068,379 B2 | 6/2006 | Sundman | |
| 7,346,998 B2 * | 3/2008 | Tadin et al. | 33/515 |
| 2002/0046472 A1 * | 4/2002 | Tadin | 33/515 |

\* cited by examiner

*Primary Examiner* — Kakali Chaki
*Assistant Examiner* — Sivalingam Sivanesan
(74) *Attorney, Agent, or Firm* — Stetina Brunda Garred & Brucker

(57) ABSTRACT

An orthotic vending machine may comprise a measuring apparatus and an orthotic fabricating apparatus. The measuring apparatus may comprises a plurality of probes capable of sensing pressure at various pixels on the underside surfaces of the person's feet at various configurations (e.g., flat plane, shoe contour, or prescriptive optimal) and determining the heights at the various pixels for the various configurations. The fabricating apparatus may lay down a plurality of discs on a base layer having different hardnesses based on the measured pressure and heights by the measuring apparatus to fabricate customized orthotics. Alternatively, the fabricating apparatus may form the customized orthotic via solidifying a polymerizeable material in a honeycomb structure based on the measured pressure and heights by the measuring apparatus. As a further alternative, the fabricating apparatus may form the customized orthotic via milling orthotic blanks based on the measured pressure and heights by the measuring apparatus. The orthotic vending machine may be placed in shoe retail shops such that shoe purchasers may purchase a shoe and a customized orthotic during one visit to the shoe store.

2 Claims, 27 Drawing Sheets

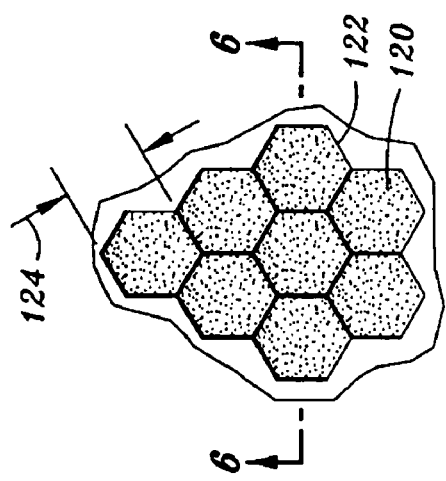
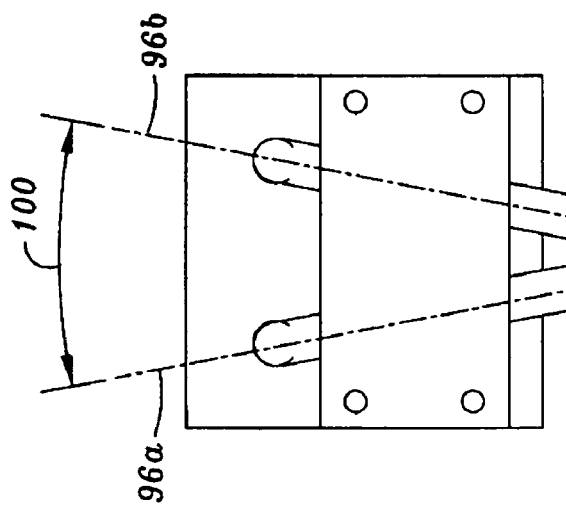
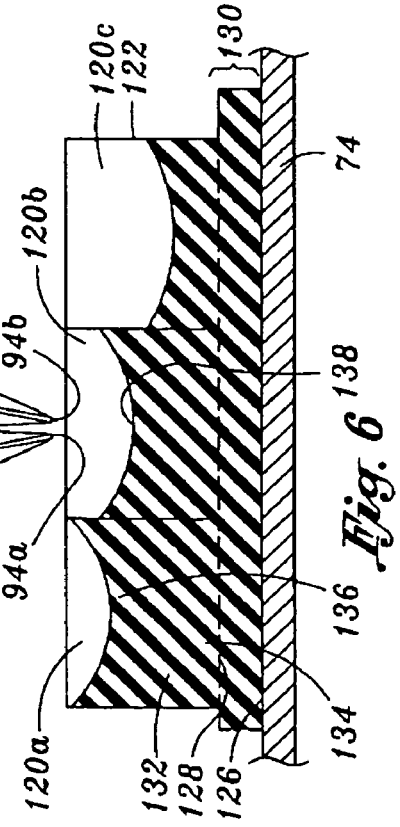
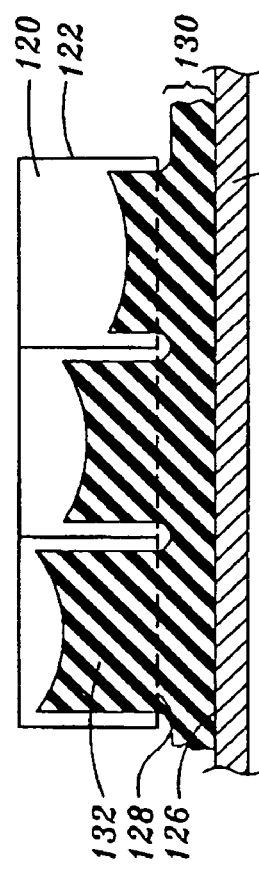

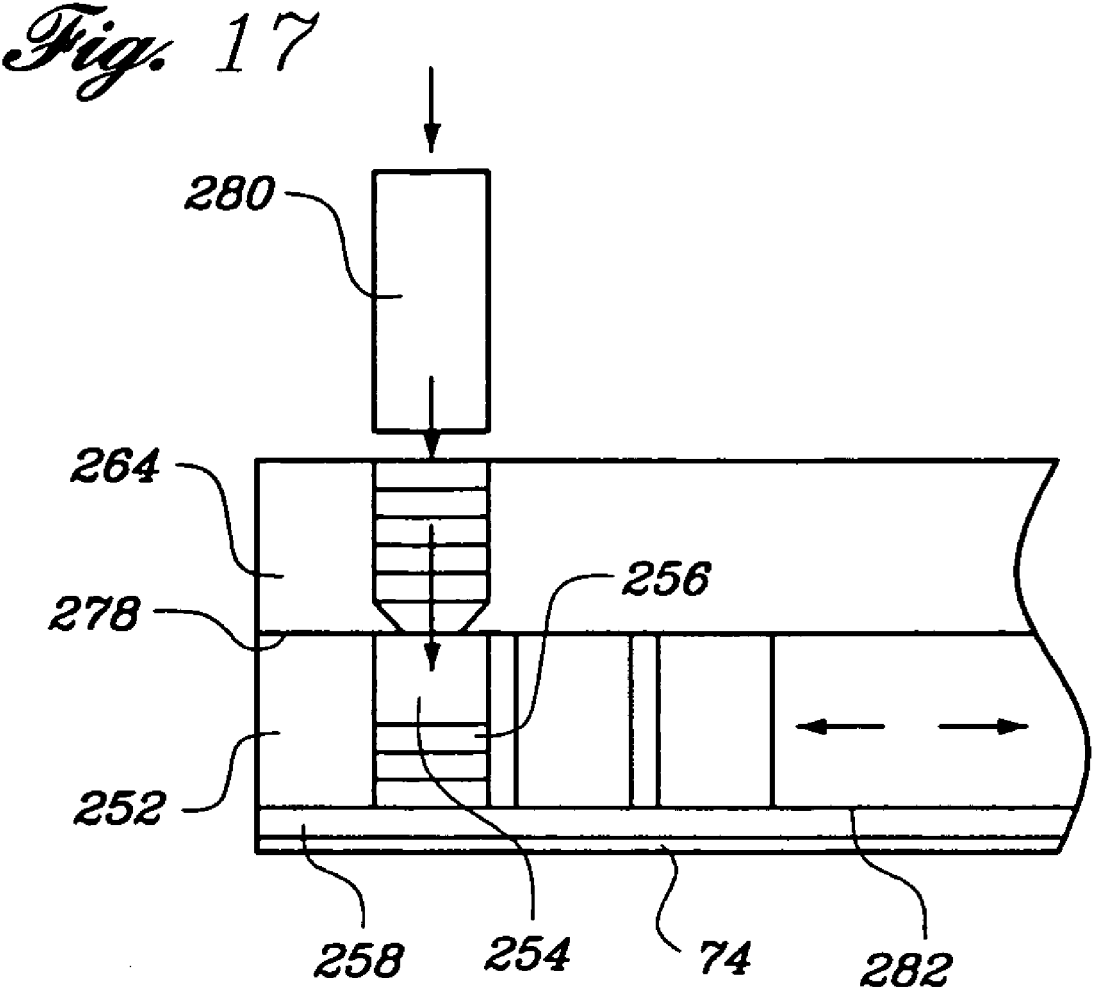

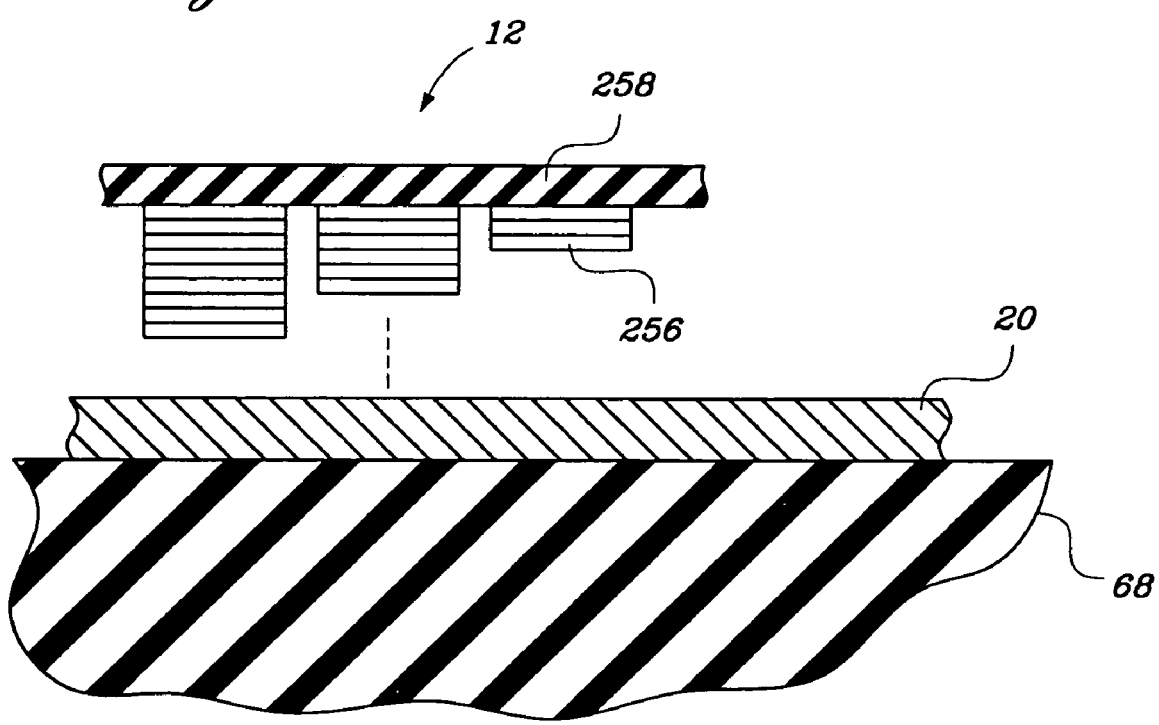

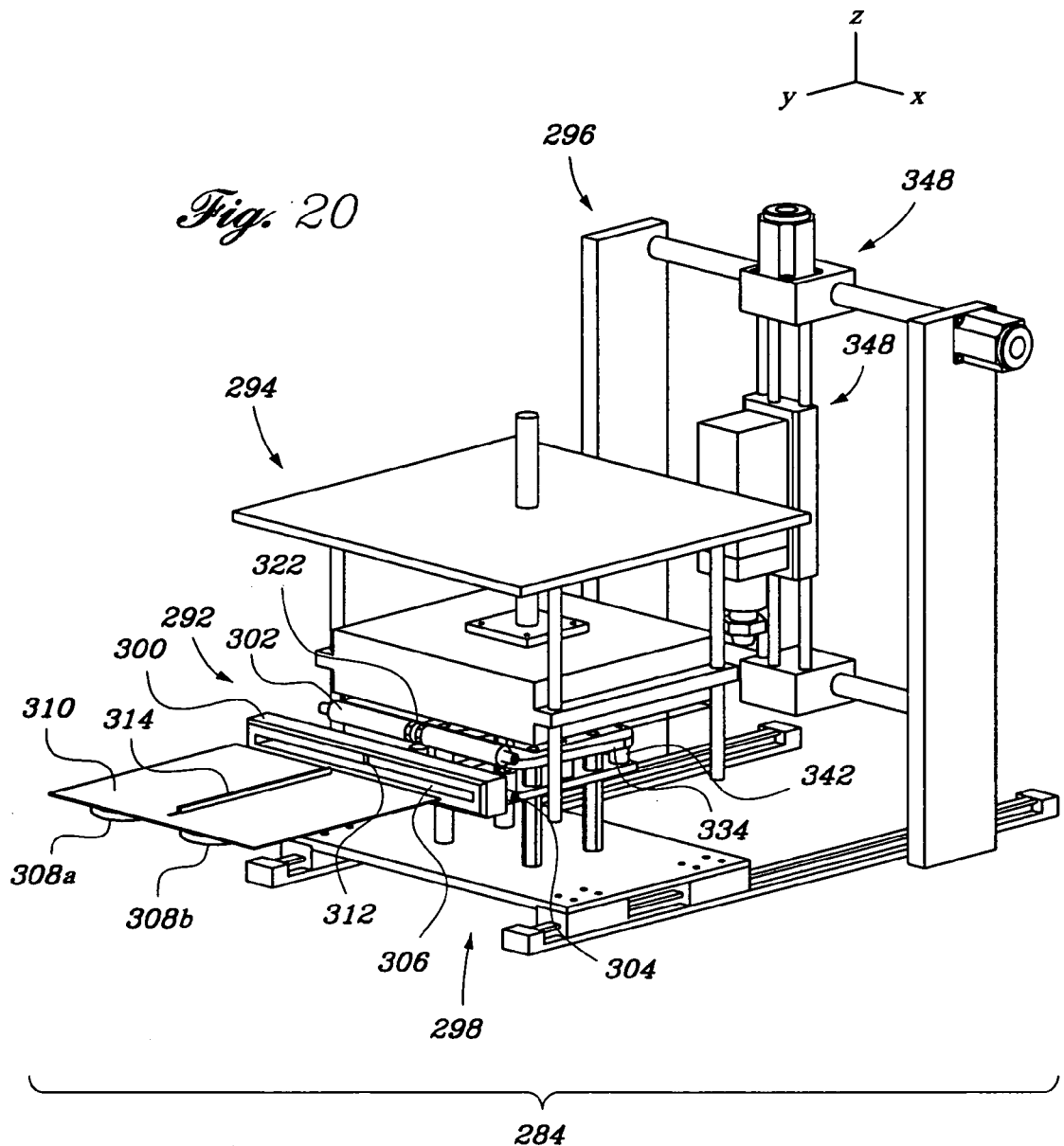

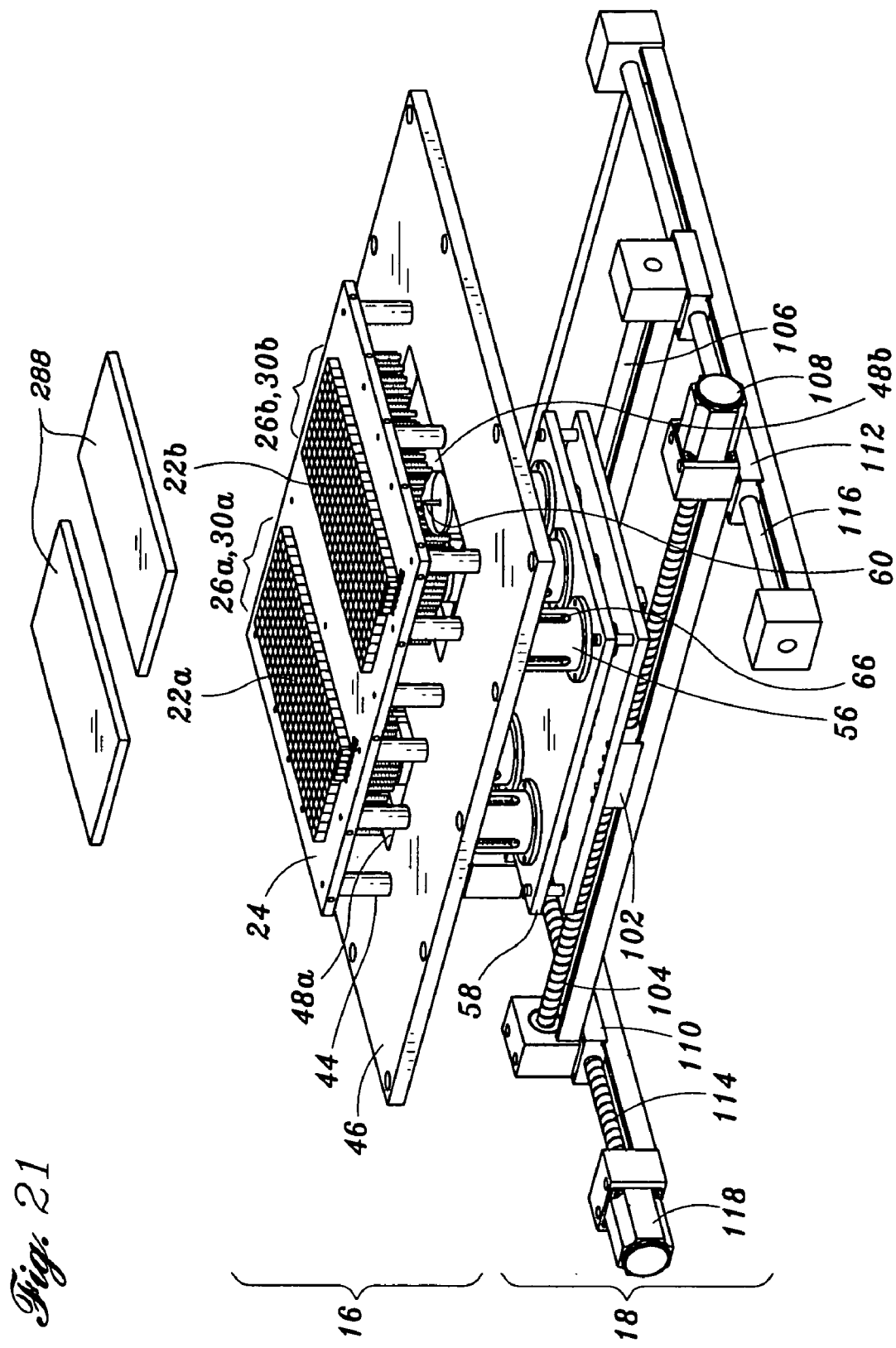

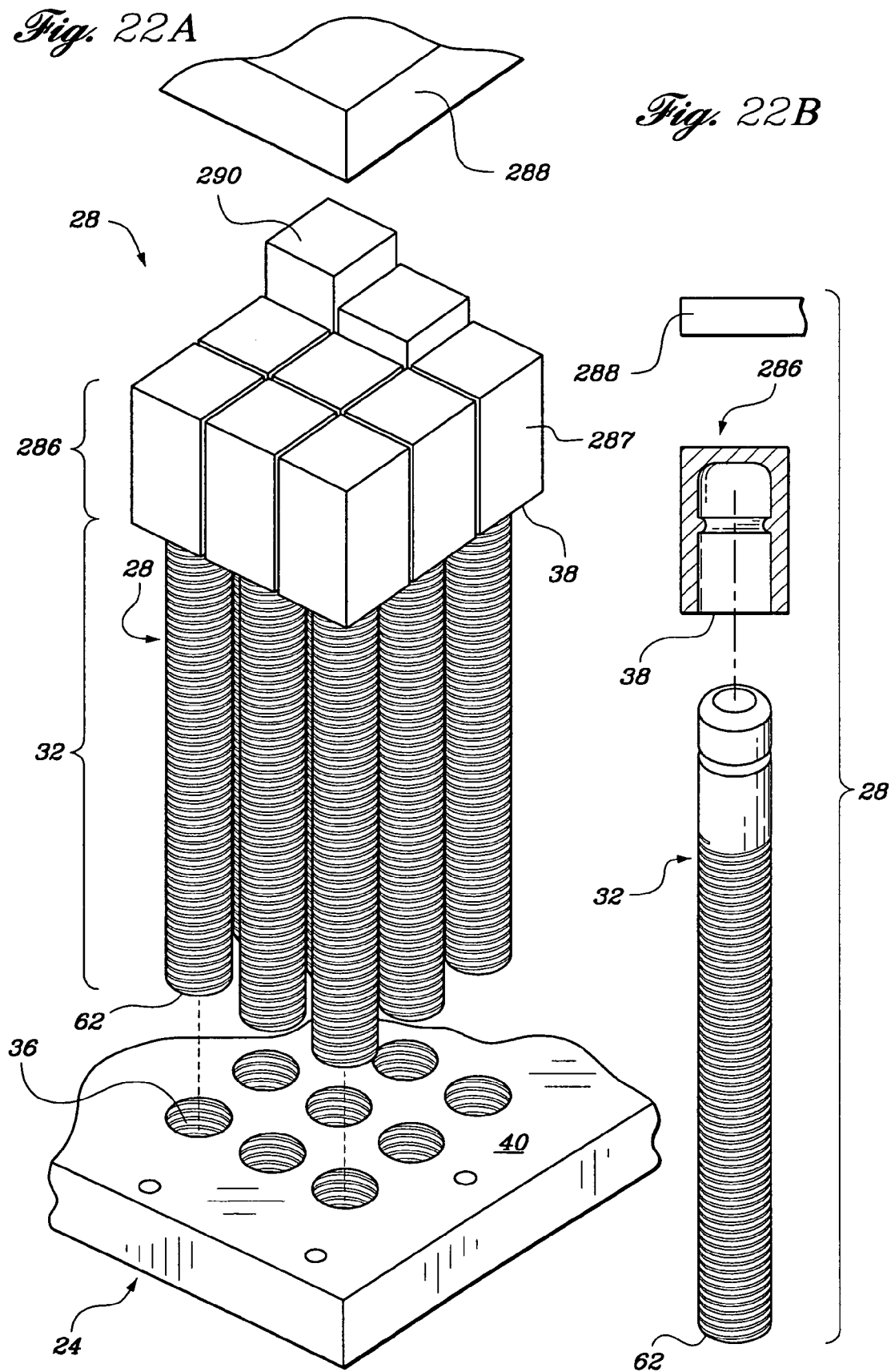

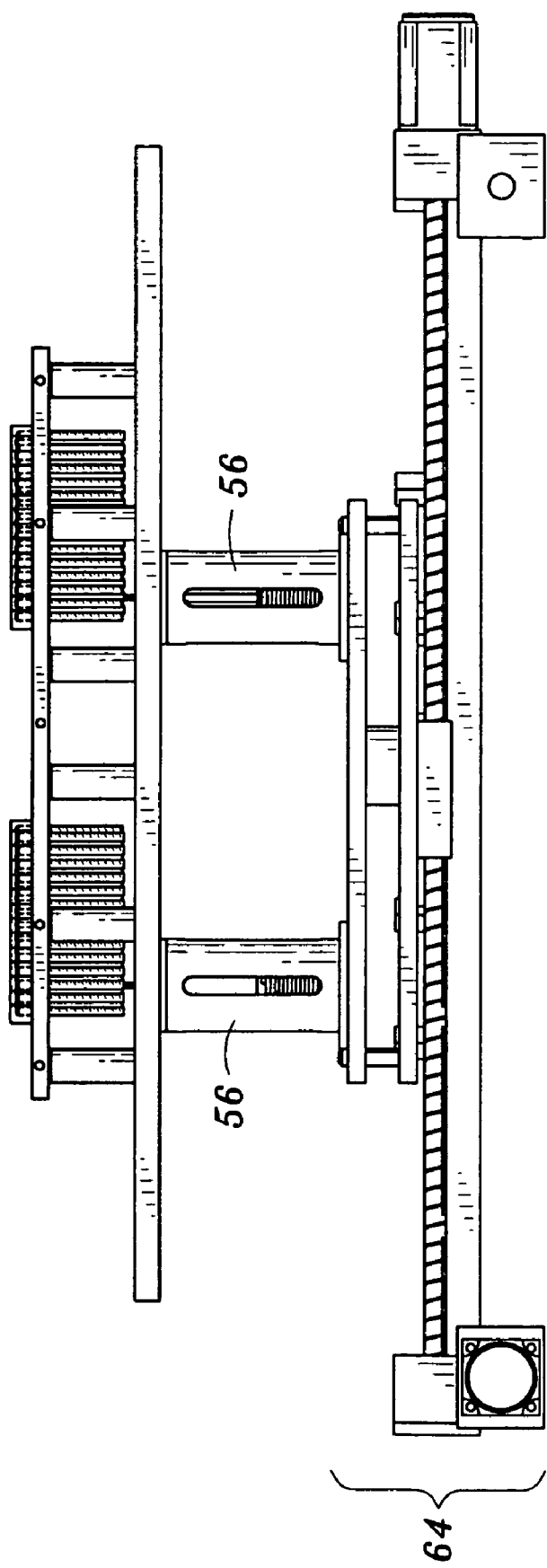

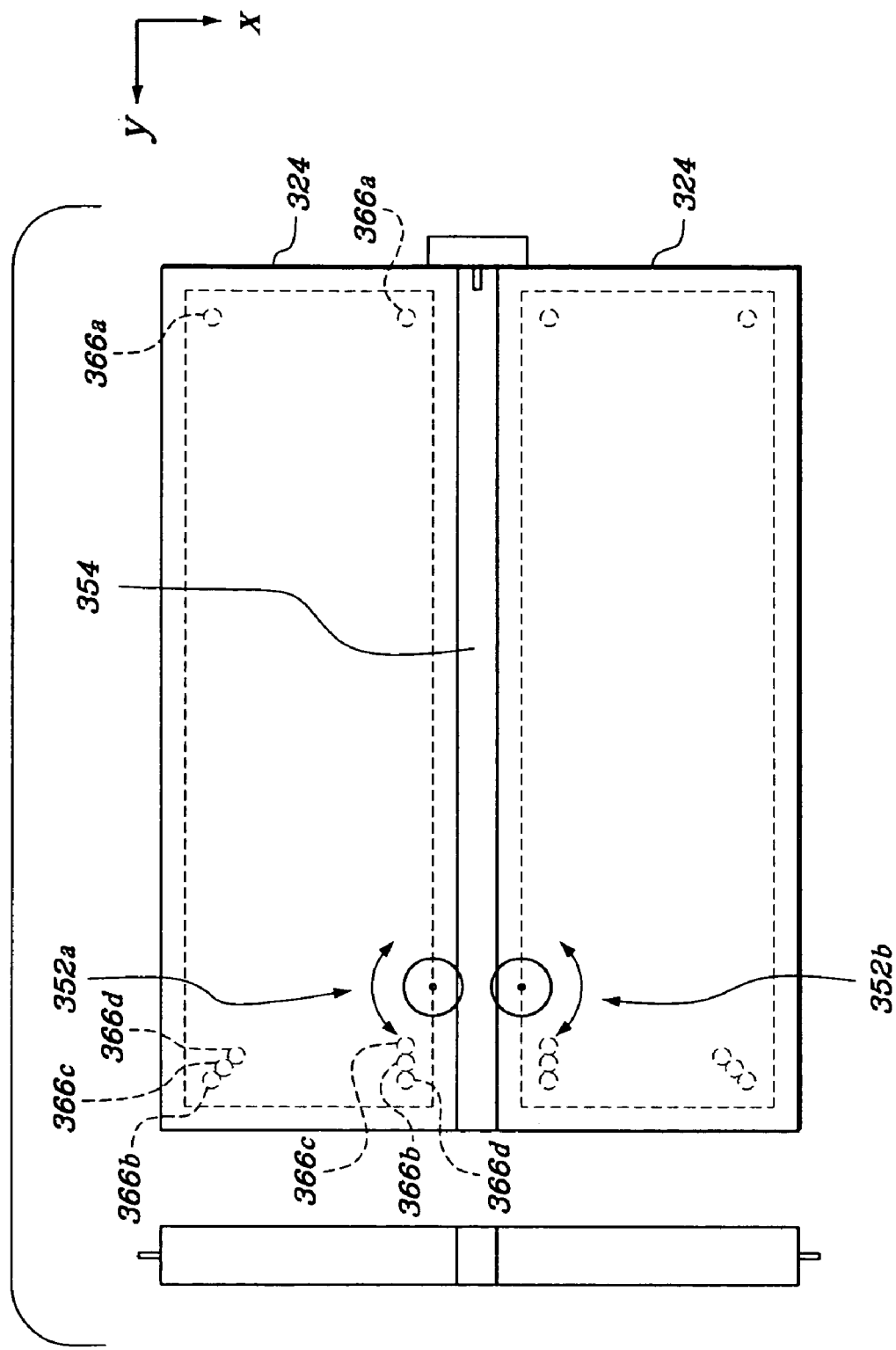

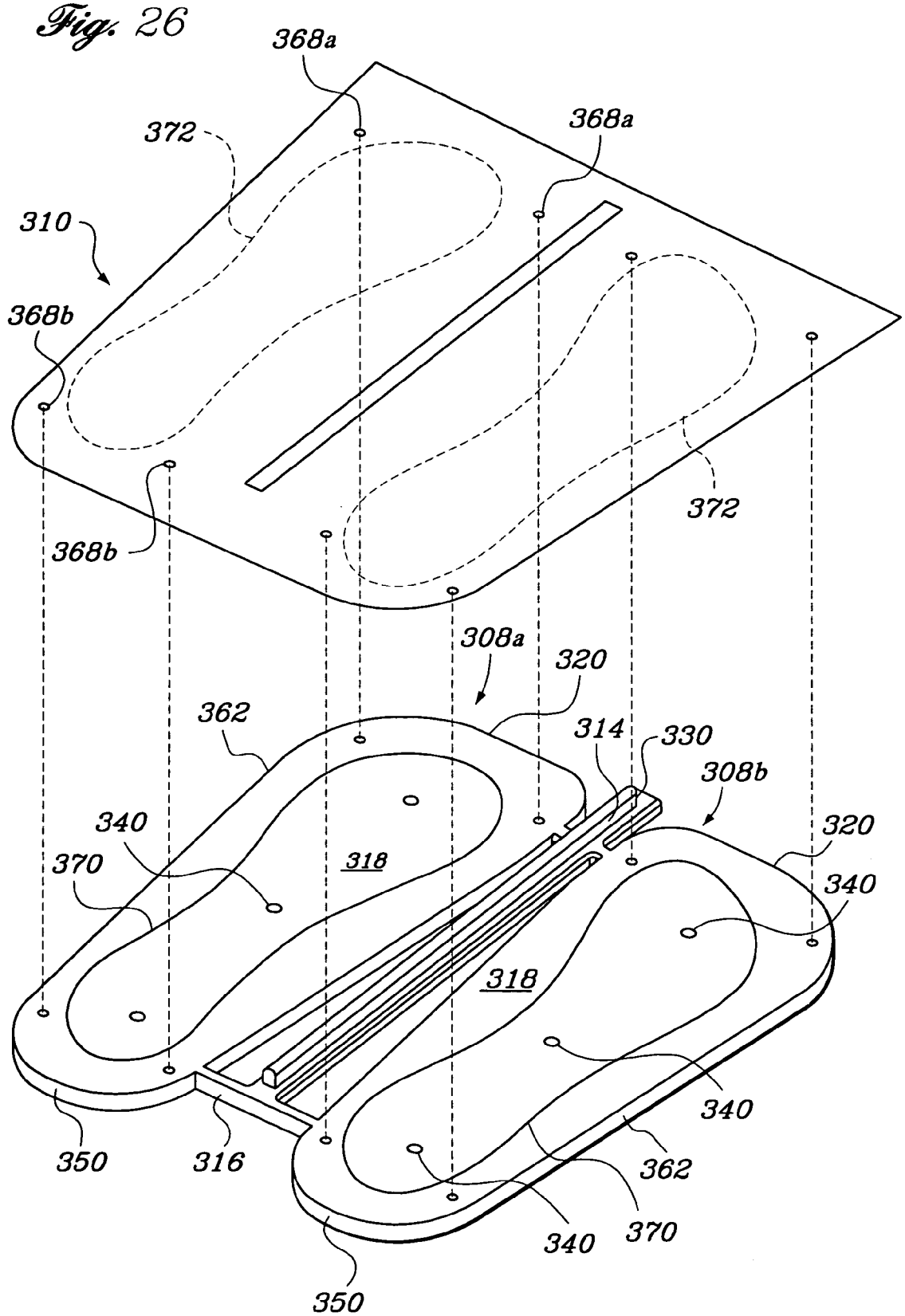

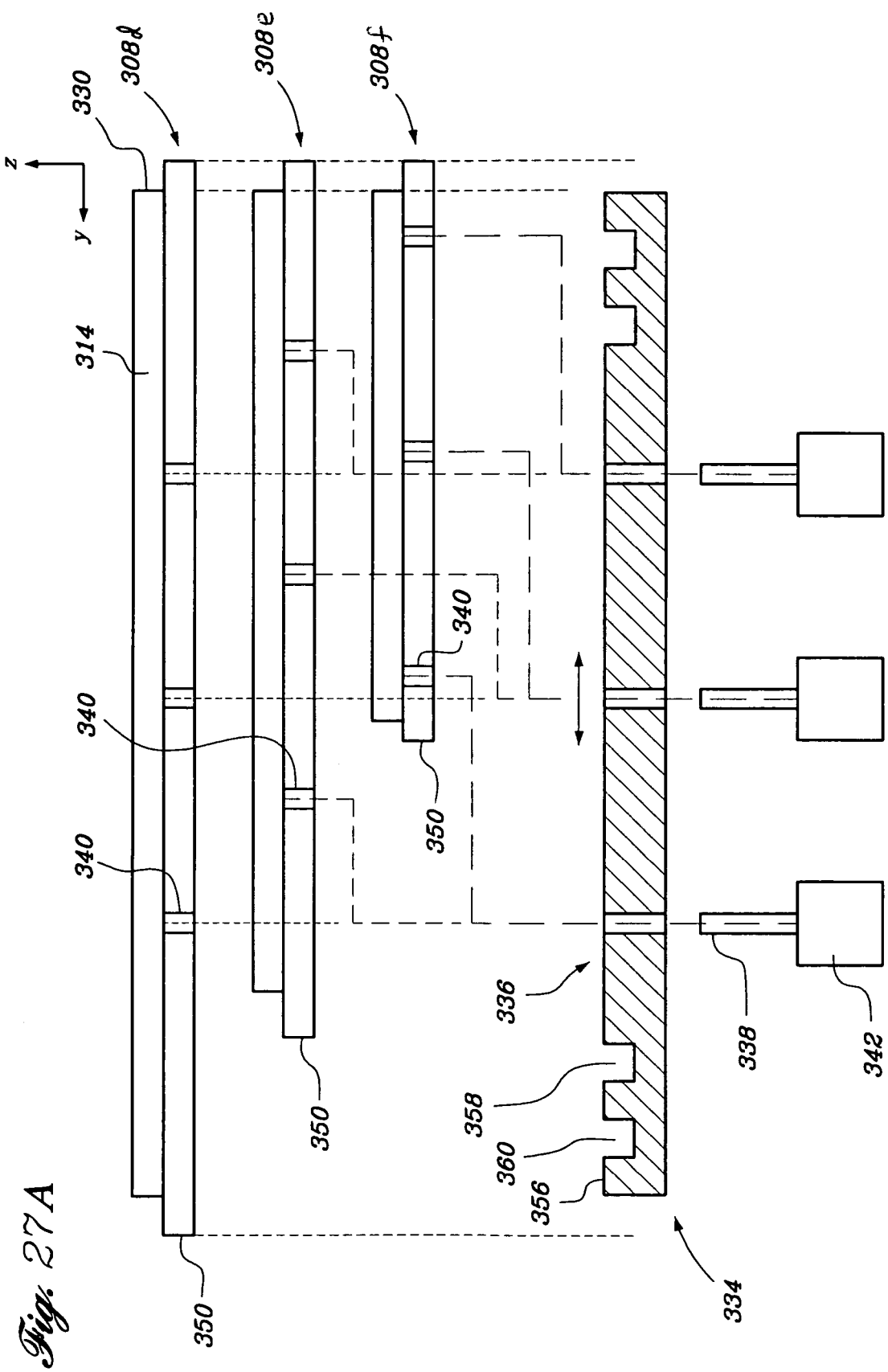

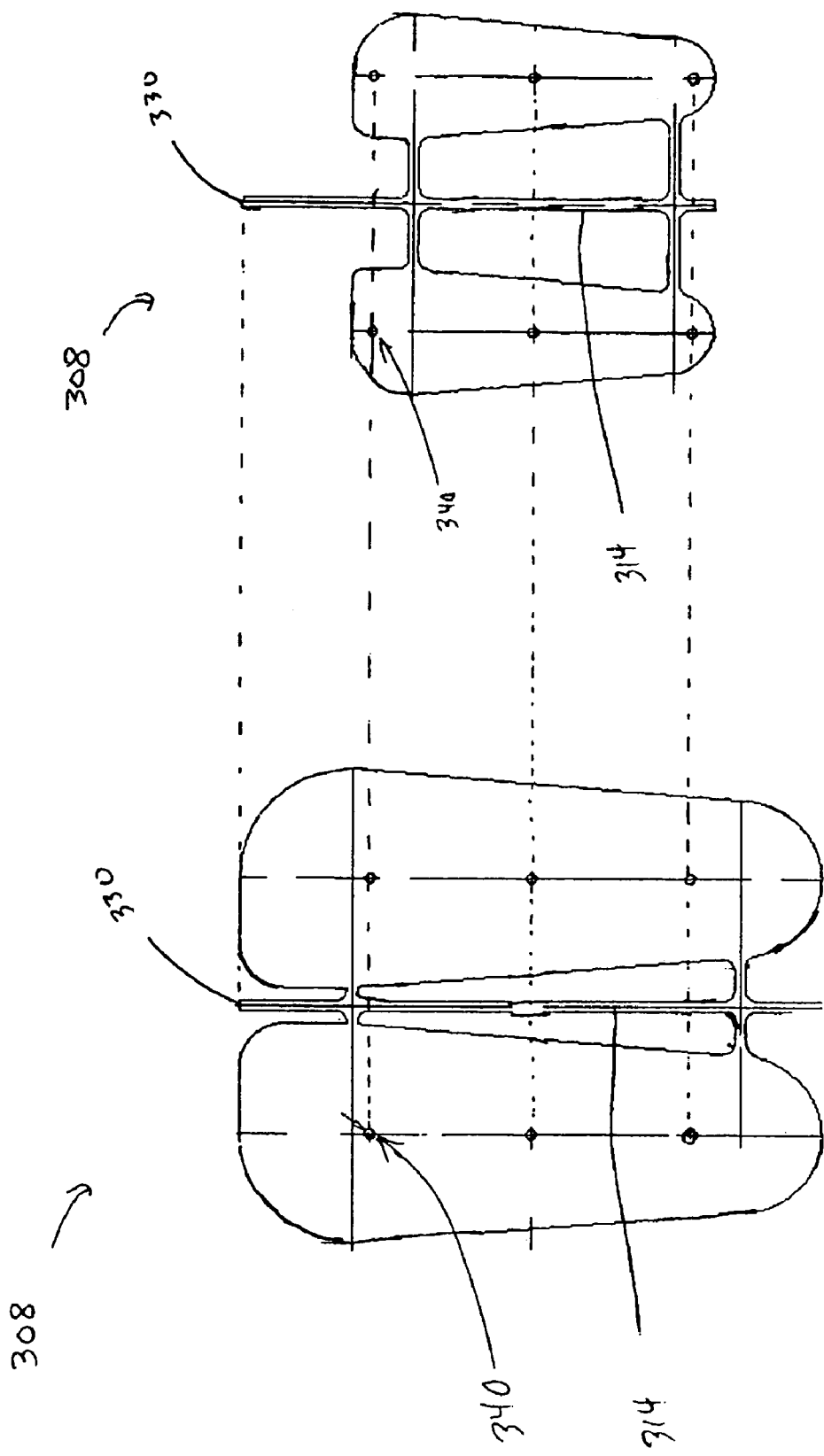

INTERACTIVE ON-DEMAND ORTHOTIC VENDING MACHINE AND METHOD OF PRODUCING ORTHOTIC INCLUDING DISC VERSION

CROSS-REFERENCE TO RELATED APPLICATIONS

This application claims the benefits of U.S. Provisional Patent Application No. 60/709,878, filed Aug. 19, 2005, the entire content of which is incorporated herein by reference. Also, this application claims the benefits of U.S. Provisional Patent Application No. 60/793,446, filed Apr. 20, 2006, the entire content of which is incorporated herein by reference.

STATEMENT RE: FEDERALLY SPONSORED RESEARCH/DEVELOPMENT

Not Applicable

BACKGROUND

The present invention relates to an orthotic vending machine, a method of measuring a pressure distribution on underside surfaces of a person's feet, a method of fabricating orthotics, a method of marketing orthotics in a retail environment, and a process of delivering custom products (e.g., customized orthotics, etc.) at the Point of Purchase.

The human foot is an engineering marvel having an intricate biomechanical composition of twenty-six bones, thirty-three joints and a complicated arrangement of muscles and ligaments. The bones, joints, and muscles intricately cooperate with each other to propel the person over an average of 100,000 miles during the person's life. Unfortunately, such repetitive and demanding use of the foot magnifies any minor foot problem into a major issue.

Foot problems affect the person's comfort level while standing, walking, or running. Moreover, foot problems may affect other areas of the person's body. For example, foot problems may affect the person's posture over a long period of time. Additionally, pain or injury may appear in the person's feet, ankles, shins, knees, hips or back.

Over-the-counter orthotics may be purchased to address foot problems. Unfortunately, over-the-counter orthotics do not appropriately resolve most foot problems. Moreover, the foot problems that over-the-counter orthotics do resolve are not always resolved effectively. Many foot problems are not effectively resolved using over-the-counter orthotics because over-the-counter (OTC) orthotics are typically designed for the average foot and do not take into consideration the wide degree of variance in foot structure, contour, gait, pronation, and supination unique to each person.

A large population does not fit within the average category, and over-the-counter products do not effectively address the foot problems of these users. Even if there is an OTC product that works for an individual finding it is a challenge since there are so many products to choose from.

Furthermore, not only are our feet unique compared to everyone else, our own two feet maybe different thereby necessitating a different orthotic for each foot. Simply put, each person needs a customized orthotic for each foot to redistribute pressures applied to the underside surfaces of the person's feet based on the unique combination of foot to foot differences, foot contour, body weight, life style, and other factors.

In the alternative, a person may purchase customized orthotics from a podiatrist. The podiatrist may form a mold of the person's feet or take an electronic contour reading. The mold/reading is sent to an orthotics manufacturer for fabrication. The orthotic manufacturer may fabricate the customized orthotics based on the mold/reading and send the fabricated orthotics to the doctor or directly to the patient. Unfortunately, customized orthotics may be cost and time prohibitive. Customized orthotics take approximately one to eight weeks to manufacture and deliver to the patient. Moreover, customized orthotics are costly, from several hundred dollars to $1,200.

Accordingly, there is a need in the art for an improved method of fabricating orthotics and providing orthotics to patients. There is also a need in the art for improved orthotics.

BRIEF SUMMARY

The present invention addresses the needs discussed above as well as other needs addressed below and those known in the art. An orthotic vending machine may be placed in a retail shoe store for the purpose of providing the shoe purchaser with a pair of orthotics within about ten (10) to fifteen (15) minutes such that the user may simultaneously purchase 1) a pair of shoes and 2) a pair of orthotics customized to fit the purchased shoes and the user's feet. By way of example and not limitation, a user may purchase shoes from a shoe store. Unfortunately, a manufacturer's inserts (insoles) provided with the purchased shoes may be sub-optimal for the user because the manufacturer's inserts (insoles) may not bring the distribution of pressure on the underside surfaces of the user's feet to optimal biomechanical positioning. For example, the arch regions of the manufacturer's insert may be too hard, too soft, too high or too low for the user thereby applying too much or too little pressure under the arches of the user's feet. Fortunately, the user may purchase a pair of customized orthotics with the orthotic vending machine to optimally redistribute the pressures on the underside surfaces of the user's feet. Each vended orthotic may be disposed on top of the manufacturer's shoe insole to optimally redistribute the pressure applied to the underside surfaces of the person's feet. Alternatively and preferably, the manufacturer's inserts (insoles) may be discarded, and each vended orthotic may be disposed on top of an upper surface of the shoe's soles. Alternatively, each vended orthotic may be disposed between the manufacturer's insole and the shoe's sole. Based on various factors, e.g., (selected shoe, etc.), the orthotic vending machine may recommend one of the three placements and/or inform the customer why such placement is recommended. The same process can be used for pre-owned shoes in a doctors office, a clinic, or virtually any place one may wish.

In the operation of the orthotic vending machine, the user may stand upon platforms of the vending machine. The vending machine may then measure the pressure distribution to the underside surfaces of the user's feet at small pixilated areas thereof. After the customer selects the shoe type, style and manufacturer the pressure sensing pixels are moved into position to emulate the manufacturer's insole contours. The vending machine then displays the changes in foot pressure distribution based on the shoe selected. Next, the customer pushes a button and the machine moves the pixels in accordance to a prescriptive algorithm that will equalize pressure under all aspects of the foot. This will allow the customer to effectively feel what the new shoe insert/orthotic will feel like. In addition to being able to feel the effects of the potential new insert/orthotic the customer will be able to see on the LCD touch screen a graphic display of the corrected pressure distribution effected by the prescriptive insert. Based on the measured contour heights and the measured pressure distribution, the vending machine may fabricate a pair of customized orthotics in about ten (10) to fifteen (15) minutes. Accordingly, the user may purchase a pair of shoes from a retail shoe store then purchase and take home a pair of customized orthotics in a single visit to the retail shoe store. The vending machine promotes sales of orthotics because the user does not have to wait until customized orthotics are fabricated off site which may take up to one to eight weeks, and the vended orthotics may be reasonably priced.

The orthotic vending machine measures the height contours and the pressure distribution with a plurality of probes operative to measure a height and a pressure of the underside surface of each foot of the user. The probes may include a stud and a hexagonal shaped cap. The stud may have a long cylindrical configuration. The cap may have a flat distal tip. The flat distal tip may have a transducer attached thereto to sense pressure. The aggregate of flat distal tips forms the platforms. The studs may be sized and configured to be received into a plurality of apertures formed in a support plate. The apertures may be threaded, and the studs may be threaded so as to be threadably insertable into the threaded apertures. The plurality of apertures and the plurality of probes may be divided into two (2) sets of apertures and probes. In particular, a first left set of probes and apertures may be disposed approximately eighteen (18) inches apart from a second right set of probes and apertures. The distance between the first and second sets of probes and apertures may be varied based upon the average foot width stance of the user.

In operating the vending machine, the flat distal tips may be vertically traversed by rotating the stud into and out of the apertures. The studs may be rotated such that the aggregate of flat distal tips (i.e., the platforms) forms a flat surface. The user may stand on the platforms with the left foot over the first set of probes and the right foot over the second set of probes. The transducers may sense the pressure on the underside surfaces of the user's feet to obtain mapped pressure distributions regarding how the underside surfaces of the user's feet supports the weight of the user.

The user may then input the manufacturer and model of shoes, which the user has purchased, will purchase, or is thinking about purchasing. The vending machine may simulate the feeling of the shoes by retrieving information relating to inner surface contours of the inputted shoes and traversing the probe distal tips to simulate the retrieved inner surface contours. This provides the user with an idea of how the purchased shoes will feel without customized orthotics. At this position, the transducers may map a pressure distribution of the underside surfaces of the user's feet. Thereafter, the vending machine may then traverse the probes to optimize the distribution of pressure on the underside surfaces of the person's feet to accomodate optimal biomechanical positioning. This provides the user with an idea of how the purchased shoes will feel with customized orthotics. The probes are vertically traversed until the pressure distribution to the underside surfaces of the user's feet meets with the machines diagnostic prescriptive algorithym selected for that particular individual. The information related to the inner surface contours of the selected shoes, the vertical traversal of the probes to bring the pressure distribution to optimal biomechanical positioning, and the associated mapped pressure distribution at the various positions of the probes may be used to calculate a contour and a hardness of the vended orthotics.

If the user decides to purchase customized orthotics, then a computer program of the vending machine may calculate a specific contour, thickness and a hardness of the customized orthotics to optimally redistribute the pressure on the underside surfaces of the person's feet based on the sensed pressure distribution and the sensed height contours of the underside surfaces of the person's feet.

The computer may then command an orthotic molding apparatus (first or second version) or a milling apparatus to fabricate the customized orthotics based on the calculated thickness and the calculated hardness thereof. In a first version of the orthotic molding apparatus, the same may comprise a polymerizable material delivery system, a plurality of cavities and a fabrication plate. The polymerizable material may be a two (2) part silicone, polyurethane or other comprising of a resin and a catalyst. The delivery system may have a resin reservoir and a catalyst reservoir which are respectively fillable with resin and catalyst. The resin reservoir may be connected to pumps to deliver the resin to outputs of resin nozzles traverseably disposable above each of the plurality of cavities. The delivery system may also have a catalyst reservoir fillable with the catalyst. The catalyst reservoir may be in fluid communication with pumps operative to deliver the catalyst to outputs of catalyst nozzles traverseably disposable above each of the plurality of cavities. The outputs of the resin and catalyst nozzles may have an elongate thin configuration to deliver respective thin films of the resin and the catalyst to each of the plurality of cavities. The outputs of the resin and catalyst nozzles may be immediately adjacent to each other such that the resin thin film and the catalyst thin film may be sufficiently mixed together when disposed in the cavity.

The computer may command the nozzles and the pumps to deliver a specific amount and ratio of resin and catalyst to each of the pluralities of cavities based on the calculated thickness and calculated hardness of the customized orthotics. When the mixed resin and catalyst is cured, a plurality of columnar pillars is formed which are held together by a thin film or layer at bottom portions of the plurality of columnar pillars. In particular, as the cavities are filled with the resin and catalyst, a small amount of mixed resin and catalyst squeezes out to adjacent cavities forming the layer or film. The plurality of cavities may be referred to as a honeycomb.

More particularly, the fabrication plate may be disposed about 0.030 inches below a lower surface of the honeycomb. The mixed resin and catalyst fill the cavity, and a small portion of the mixed resin and catalyst is disbursed onto the fabrication plate spreading under adjacent cavities. As each of the cavities are filled with the mixed resin and catalyst, the small portions of mixed resin and catalyst disbursed on the fabrication plate forms the film or layer that holds the plurality of columnar pillars in fixed relationship to each other.

As the polymerizeable material is being polymerized, the material slightly shrinks so as to move away from cell walls of the cavities. After the polymerizeable material has been polymerized, the fabrication plate is lowered away from the honeycomb to remove the polymerized material (i.e., plurality of columnar pillars) from the honeycomb. A first set of cavities may have a plurality of columnar pillars in the general shape of the left foot, and a second set of cavities may have a plurality of columnar pillars in the general shape of the right foot. As a final step, a knife may cut an outer periphery of the left orthotic and the right orthotic. Additionally, a fabric or other material cover may be attached to the orthotic. This material may also be infiltrated with a silver oxide or other bacteriocidal/fungicidal ingredient for the purpose of odor control and antifingal control. Thereafter, the orthotics may be presented to the customer.

It is preferable to coat the cell walls of the honeycomb molding plate with nickel Teflon such that the polymerisable material does not stick thereto and may easily slide out of the cavities of the honeycomb. It is also preferable that the polymerized material be pushed out of the cavities.

Alternatively, a second version of the orthotic molding apparatus may include two separate orthotic manufacturing units. The first orthotic manufacturing unit may fabricate an orthotic for a left foot of a person. Also, a second orthotic manufacturing unit may fabricate an othotic for a right foot of a person. The orthotic manufacturing unit may fabricate the orthotic by laying a plurality of discs on a base layer (e.g., fabric, and the like) and permanently attaching the discs to each other as well as to the base layer. The discs may be selectively attached to the base layer with respect to position, number of discs and hardness. Each of the orthotic manufacturing units may have a hopper, tube plate, dispensing plate, honeycomb, the base layer and the fabrication plate. The tube plate may be fabricated with at least three rows of a plurality of tubes. The tubes of each row may be longitudinally stacked in an offset manner to increase the longitudinal density of the number of tubes per row of tubes. One hopper may be placed over each row of tubes. Each hopper may contain a plurality of discs having the same hardness. Also, the discs in the different hoppers may have a different hardness. For example, a left hopper may contain a plurality of soft discs. A middle hopper may contain a plurality of medium hardness discs. A right hopper may contain a plurality of hard discs.

The hopper may have four sidewalls which define an inner volume. The hopper may have a top cover which is removably engageable to a top of the four sidewalls. A bottom of the hopper may have a plurality of apertures which are sized and configured to receive a respective one of the tubes. The hopper may be filled with discs and the top cover placed on the hopper to prevent any of the discs from falling out of the hopper during operation.

With the hopper, tube plate and dispensing plate in the position shown in FIG. 11, the hopper is rapidly traversed vertically in the plus and minus Y direction. As the hopper is moved up (see FIG. 12) and down (see FIG. 13), the discs within the hopper begin to fill up each of the tubes, as shown in FIG. 12. When the tubes are filled with discs, the hopper's vertical reciprocal movement is halted. At this point, the tubes of each of the rows of tubes have a plurality of discs filled therein. A different hardness disc is filled in each of the row of tubes. The dispensing plate is then traversed in the negative Z direction until a plurality of apertures of the dispensing plate is aligned to the rows of tubes in the x-direction. As the dispensing plate is traversed in the negative Z direction, the discs within the tubes slide on a top surface of the dispensing plate. When the apertures of the dispensing plate is aligned to the tubes in the x-direction, the tube plate is traversed in the negative X direction (see FIGS. 14 and 15) until the tubes are vertically aligned to the apertures, as shown in FIG. 15. At this point, the plurality of discs within the tubes slide down into the apertures of the dispensing plate. A bottom edge of the apertures of the dispensing plate has an internal inwardly directed edge which prevents the discs from falling out of the apertures of the dispensing plate. The tube plate is then traversed in the positive X direction and the dispensing plate is then traversed in the positive Z direction, as shown in FIG. 11.

The plurality of discs are then displaced into a honeycomb and on a base layer by pushing the discs through a bottom surface of the dispensing plate via pins, as shown in FIGS. 11 and 16. Once the discs fall through the bottom surface of the dispensing plate, the discs are received into an aperture of the honeycomb and on a base layer, as shown in FIG. 17. The base layer is disposed on a fabrication plate. The fabrication plate and a bottom surface of the honeycomb does not have a gap as described in the first version of the orthotic molding apparatus. Rather, the base layer contacts the bottom surface of the honeycomb such that the discs are not permitted to move out of alignment with the aperture of the honeycomb. The honeycomb and base layer are traversed in the positive and negative X direction until the apertures of the honeycomb are filled with the appropriate number of discs and hardness.

Each of the apertures of the honeycomb may be filled with one or more discs of the same or different hardness. As such, each of the apertures of the honeycomb may be filled with one or more soft discs, one or more medium hardness discs, one or more hard discs, or any combination thereof. By this manner, each of the apertures of the honeycomb may be filled with two or more different hardness discs to fabricate a customized orthotic.

The orthotic vending machine determines the number of discs and the hardness of the discs to insert into each aperture of the honeycomb based on the measured height contour and pressure distribution of the underside surface of the person's foot. Also, the orthotic vending machine builds the orthotic based on the determined thickness and hardness with discs via the method described herein.

In FIG. 11, although only one pin is shown, a plurality of pins may be positioned above the apertures of the dispensing plate. Each of the pins may push down the disc within the dispensing plate. The pin may be accurately vertically traversed such that the pin may displace only a selected number of discs into the apertures of the honeycomb.

After the correct number of discs of a particular hardness has been filled within the appropriate apertures of the honeycomb, the discs are permanently attached to each other as well as to the base layer. By way of example and not limitation, each side of the disc may have an RF energy activated adhesive. After the correct number and type of discs have been disposed within the apertures of the honeycomb, the discs and the base layer may be exposed to RF energy which permanently attaches the discs to each other and to the base layer. A final cut in the shape of the inner periphery of the person's shoe is made to the base layer and discs such that the customized fabricated orthotic may be inserted in the person's shoe.

The orthotics formed in the above mentioned manner may be fabricated in an inverted manner.

In a third method of forming the orthotics which is via the milling apparatus, the same may have an entry port, laminator section and a milling section. The entry port is configured to align a near net shaped orthotic blank to the milling apparatus. The orthotic blank may be secured to a machining platen and subsequently milled via a milling head. The milling head mills the orthotic blank according to the measured pressure distribution of the underside surfaces of the user's feet to bring the user's feet to an optimal biomechanical position. After the orthotic blank is milled via the milling head, a cover layer may be adhered to the top surfaces of the left and right orthotic blanks.

The orthotics formed in the above mentioned manner in relation to the milling apparatus may be fabricated in a right side up manner.

The vending machine may also comprise of a display which is operative to display instructions to guide the purchaser or user in operating the vending machine. The display may also provide information regarding the sensed pressure distribution of the underside surfaces of the person's feet.

The computer may also have a communications port for providing a communications pathway to an offsite server, financial institution or a medical doctor (i.e., podiatrist). The server may be operative to transmit information related to the inner surfaces of a plurality of shoes to the vending machine. The server may also be operative to receive status information from a plurality of sensors attached to various components of the vending machine for the purpose of maintenance and the like. The communications port may communicate with a financial institution to debit a credit card account or bank account of the user such that the user may pay for the customized orthotics. Moreover, the communications port may provide a communications pathway to a medical doctor for on-line, virtual, or telephonic consultations. The vending machine may advertise specific products and/or refer customers to podiatrists, therapist, etc.

BRIEF DESCRIPTION OF THE DRAWINGS

These and other features and advantages of the various embodiments disclosed herein will be better understood with respect to the following description and drawings, in which like numbers refer to like parts throughout, and in which:

FIG. 5 is an enlarged top view of a plurality of cavities;

FIG. 6 is a cross sectional view of the cavities shown in FIG. 5 illustrating nozzles disposed over the cavity and a different amount of resin and catalyst in each of the cavities;

FIG. 6A is a cross sectional view of the cavities shown in FIG. 5 illustrating a cured resin/catalyst mixture wherein the mixture has shrunk after curing;

FIG. 17 is a cross sectional view of pin, dispensing plate, base layer and fabrication plate illustrating the honeycomb, base layer and fabrication plate traversable across the rows of apertures of the dispensing plate for filling any one of the apertures of the honeycomb with a different hardness disc

FIG. 19 is an enlarged view of FIG. 18A;

FIG. 20 is a perspective view of a milling apparatus;

FIG. 21 is a perspective view of a second embodiment of the measuring apparatus;

FIG. 22A is an enlarged view of the measuring apparatus shown in FIG. 21 illustrating a plurality of probes threadably inserted into a plurality of apertures of the support plate;

FIG. 22B is a front view of the probe shown in FIG. 22A wherein the probe has a stud, a cap and a pressure sensor mat;

FIG. 23 is a front view of the measuring apparatus shown in FIG. 21;

FIG. 25A is a top cross sectional view of a heating block of a laminator section;

FIG. 26 is a top perspective view of the orthotic blank used in conjunction with the milling apparatus;

FIG. 27A is a side cross sectional view of the machining platen with one of three different orthotic blanks disposable over the machining platen;

FIG. 29 is illustrates the alternative blanks shown in FIG. 28.

DETAILED DESCRIPTION

Figure 1:
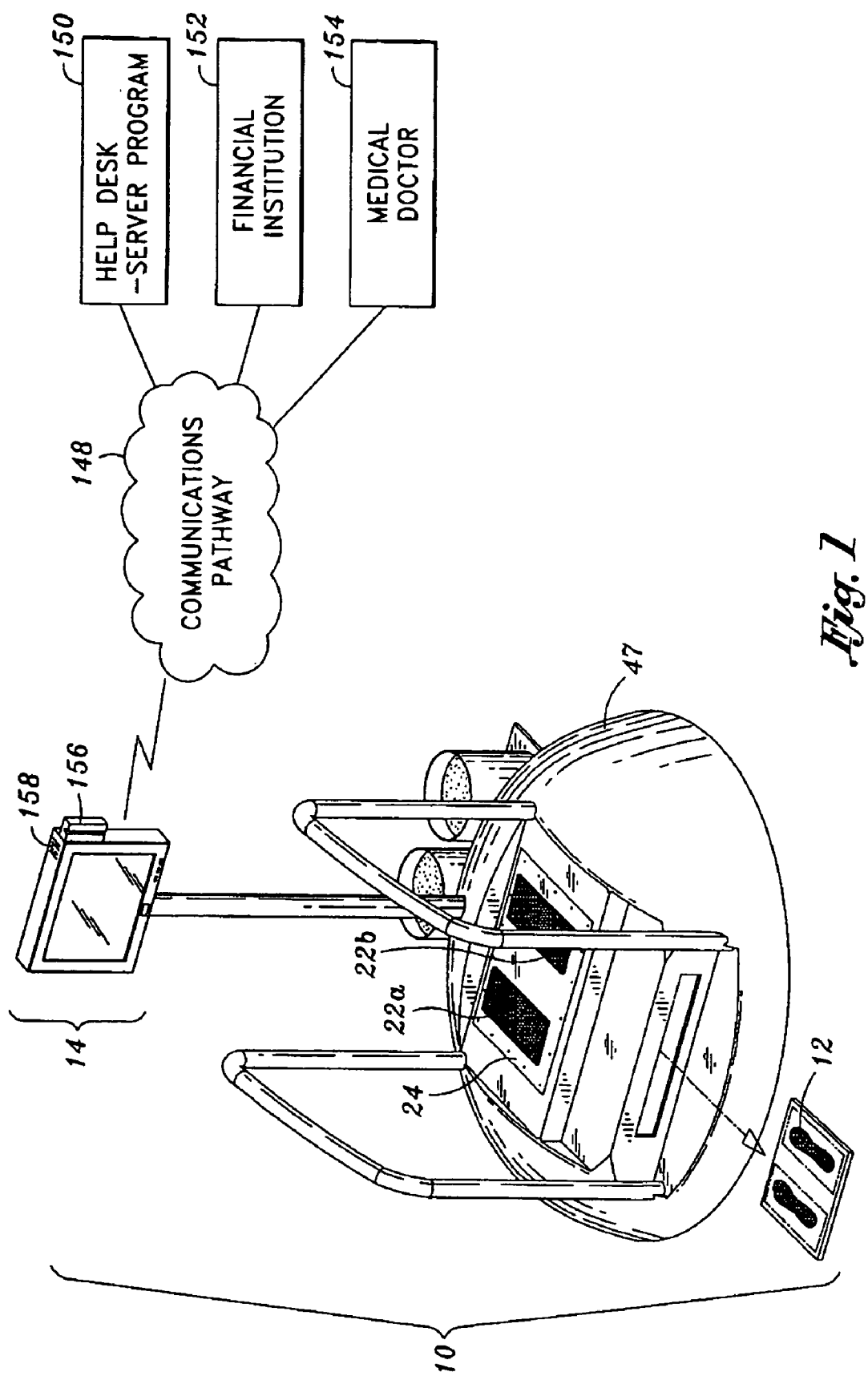
FIG. 1 is a perspective view of an orthotics vending machine wherein a computer of the machine is in communication with a server, financial institution, and/or a medical doctor via a communications pathway.

Referring now to FIG. 1, an orthotic vending machine 10 is illustrated which may measure height contours and pressure distribution of the underside surfaces of a user's feet in relationship to or in combination with the contours of the insoles of the shoes to be purchased and fabricate a pair of customized orthotics 12 based on the measured height contours and the measured pressure distribution within about ten (10) to fifteen (15) minutes. It may also do so in relationship to or in combination with the contours of the insoles of the shoes to be purchased. The short turn around time from measurement to providing the customized orthotics 12 to the user, allows a purchaser to purchase shoes and fit the shoes with customized orthotics 12 during a single visit to a retail shoe store.

The orthotic vending machine 10 may comprise a display 14, a computer, a measuring apparatus 16 (see FIGS. 2 and 21), and a molding apparatus 18 (see FIGS. 2 and 11) or a milling apparatus 284 (see FIG. 20). The shoe purchaser or user may purchase shoes (e.g., running shoes, tennis shoes, golf shoes, comfort shoes, etc.) from a retail shoe store. The shoes salesperson may then suggest that the shoes purchaser purchase a pair of customized orthotics 12 to correct any sub-optimized pressure distribution on the underside surfaces of the user's feet due to manufacturer's shoe inserts (insoles) 20 (see FIGS. 7A, 7B, and 7C; 18A, 18B, and 18C; and 24A, 24B and 24C. The shoes purchaser may use the orthotic vending machine 10 to experience how the shoes will feel without and with a pair of customized orthotics 12 to decide whether the user wants to purchase the customized orthotics 12.

Figure 2:
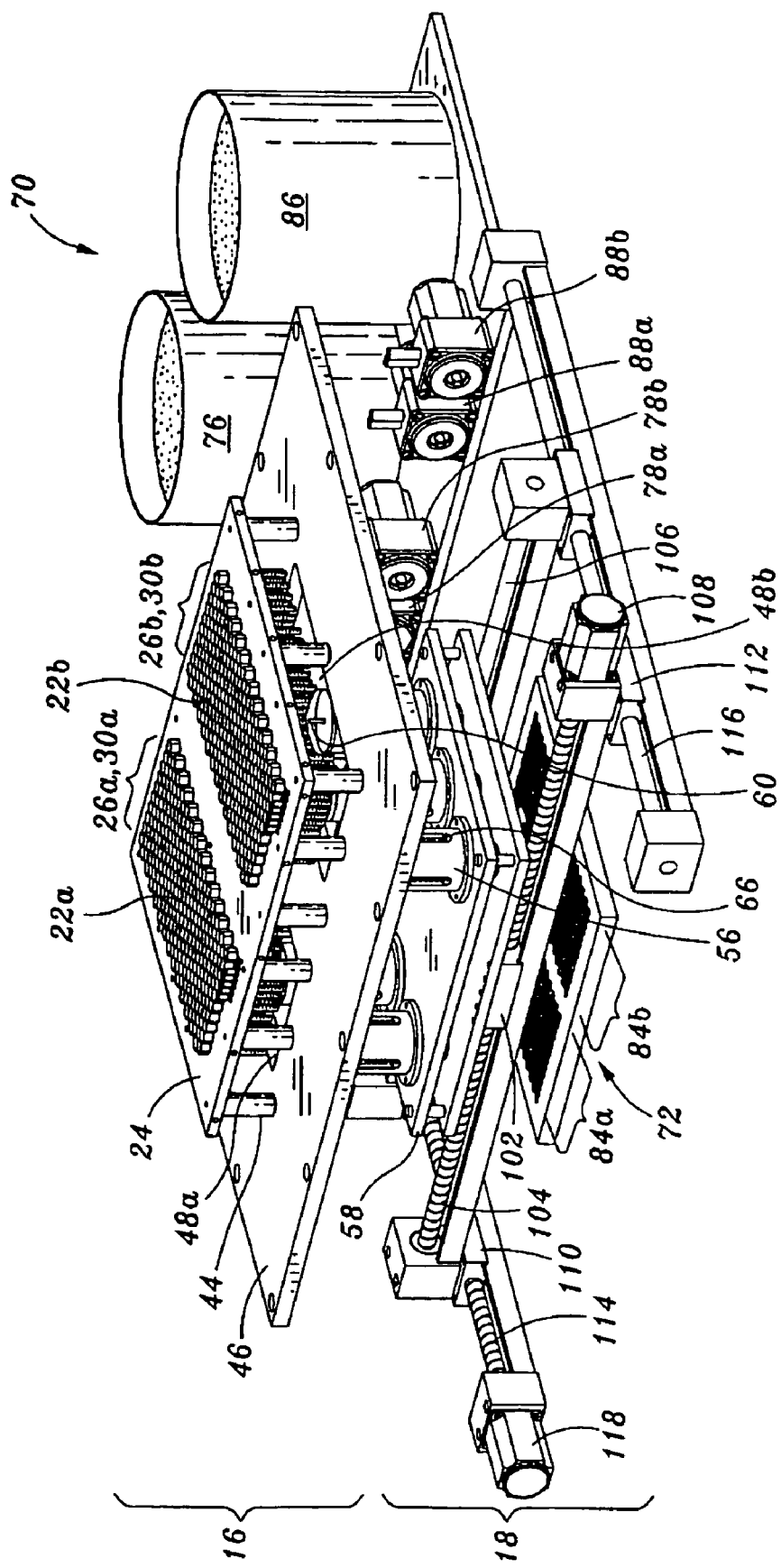
FIG. 2 is a perspective view of a measuring apparatus and a first version of an orthotic molding apparatus of the orthotics vending machine shown in FIG. 1.
Figures 2A, 2B:
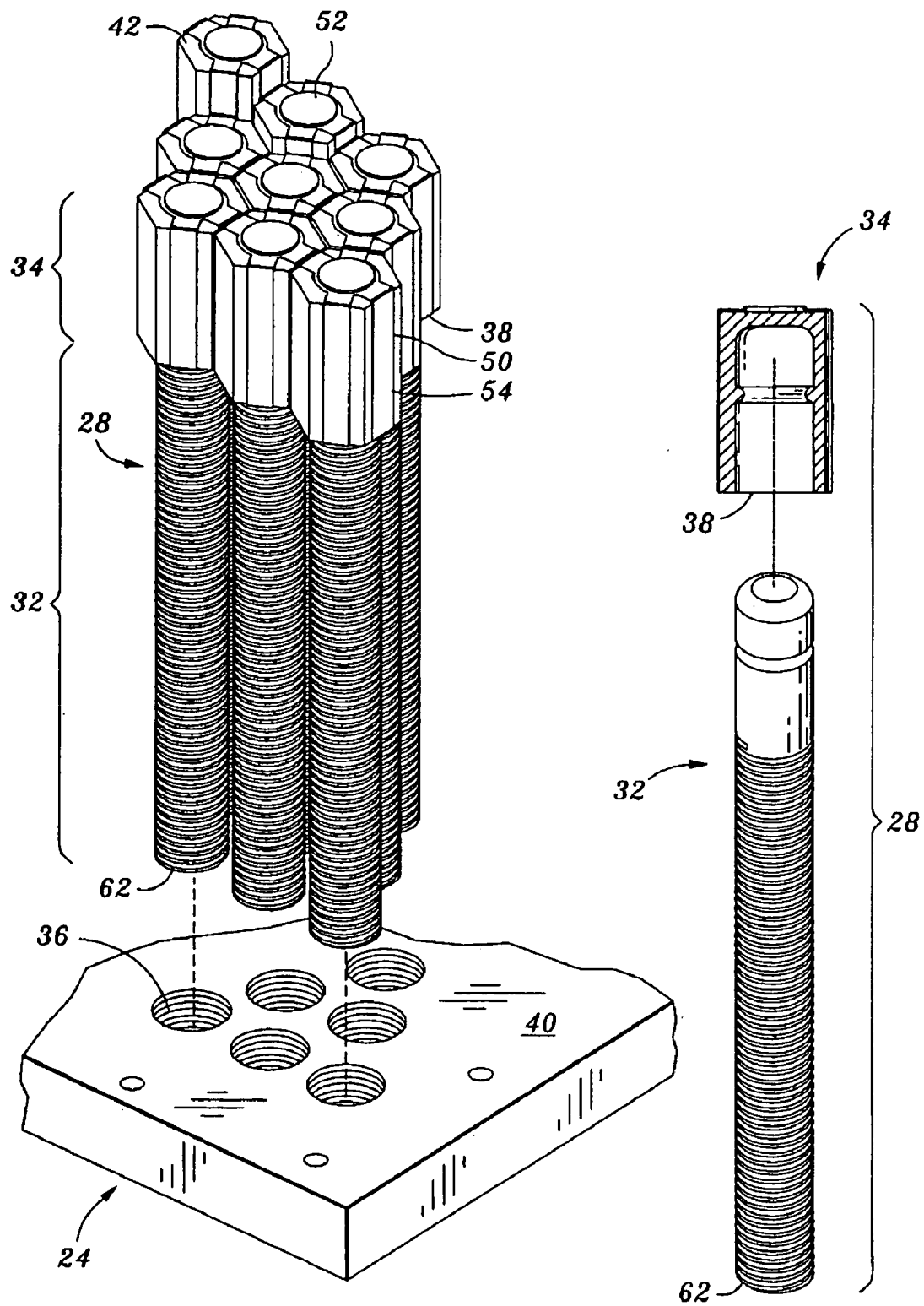
FIG. 2A is an enlarged view of the measuring apparatus illustrating a plurality of probes threadably insertable into a plurality of apertures of a support plate.
FIG. 2B is an exploded view of the probe shown in FIG. 2A wherein the probe has a stud and a cap.

The user may step onto a left platform 22a and a right platform 22b of the measuring apparatus 16 (see FIGS. 1, 2, and 21) for measuring height contours and pressure distribution of the underside surfaces of the user's feet. In particular, the measuring apparatus 16 may include a support plate 24. The support plate 24 may have a first left set 26a of apertures and a second right set 26b of apertures, as shown in FIGS. 2 and 21. Probes 28 (see FIGS. 2A and 2B) of a first left set 30a (see FIG. 2) and a second right set 30b (see FIG. 2) may each have a stud 32 and a hex cap 34 attached to the stud's upper distal end, as shown in FIGS. 2A and 2B. Alternatively, the probes 28 of the first and second sets 30a, b may each have a stud 32 and a square cap 286 attached to the stud's upper distal end, as shown in FIGS. 22, 22A and 22B, with a pressure sensor mat 288 disposed over the collective top surfaces 290 of the square caps 286. The probes 28 measure the height contours and pressure distribution of the underside surfaces of the user's feet. The studs 32 and the apertures 36 may be threaded such that the studs 32 are threadably receivable into the apertures 36. The studs 32 are threaded into the apertures 36 until a bottom surface 38 of the hex cap 34 or square cap 286 contacts an upper surface 40 of the support plate 24. Top surfaces 42 of the hex caps 34 or square caps 286 collectively form the left and right platforms 22a, b.

The apertures 36 of the first set 26a may be equally spaced apart from adjacent apertures 36. Similarly, the apertures 36 of the second set 26b may be equally spaced apart from adjacent apertures 36. The first and second sets 26a, b of apertures 36 may each comprise five hundred (500) apertures 36 evenly spread about an area of about 6 inches by about 13 inches (custom platforms may have larger dimensions). Probes 28 may be inserted into the apertures of the first and second sets 26a, b with the top surfaces 42 of the probe hex caps 34 or probe square caps 286 collectively forming the platforms 22a, b. The first and second sets 26a, b of the apertures 36 may be separated from each other to permit the user to stand over the platforms 22a and 22b with the person's left foot and right foot, respectively. Preferably, the first and second sets 26a, b of apertures 36 are about eighteen inches apart from each other. Indicia in the shape of the left foot and the right foot may be provided on the platforms 22a, b to inform the user that the user should step on top of the platforms 22a, b with his/her left foot and right foot, respectively.

As shown in FIGS. 2 and 21, the support plate 24 may be supported by a plurality of posts 44 which are selectively placed about a periphery thereof. The posts 44 may be supported on top of a cover plate 46. The cover plate 46 may be fixedly attached to a base cover 47 (see FIG. 1). The cover plate 46 may additionally have two apertures 48a, b sized and configured larger than an aggregate area of the studs 32 of the first and second sets 30a, b of probes 28, respectively.

The probes 28 may be vertically traversed between a fully retracted position to a fully extended position. The probes 28 may be traversed between the fully retracted position and the fully extended position by rotating the studs 32 clockwise or counterclockwise. Additionally, while the probes 28 are being vertically traversed, the hex caps 34 or square caps 286 do not rotate but are only vertically traversed. In particular, the hex cap 34 or square caps 286 may snap onto a distal end of the threaded stud 32, as shown in FIGS. 2B and 22B. The hex caps 34 or square caps 286 may be disposed immediately adjacent to each other. The hex caps 34 or square caps 286 may be vertically raised and lowered by rotating the stud 28 into and out of the apertures 36. The hex caps 34 or square caps 286 do not rotate with the studs 28 because the hex cap sides 50 or square cap sides 287 abut sides 50, 287 of adjacent hex caps 34 or square caps 286.

In relation to the hex caps 34, the flat top surfaces 42 of the hex caps 34 may have pressure sensors 52 (e.g., transducers) attached thereto. Each hex cap 34 may have beryllium copper 54 on external surfaces thereof and in contacting alignment with beryllium copper 54 on adjacent hex caps 34. Beryllium copper on adjacent hex caps 34 remain in electrical contact with each other due to an outward bow of the sides 50 of the hex caps. The beryllium copper 54 provides a communications pathway from each of the pressure sensors 52 to the computer such that the computer may retrieve a sensed pressure from each of the pressure sensors 52. Alternatively or in conjunction with the beryllium copper interconnection assembly, each pressure sensor may be interrogated with the use of a frequency selected RFID device placed individually or alongside each pressure sensing device.

Alternatively, in relation to the square caps 286, the collective flat top surfaces of the square caps 286 may have the pressure sensor mat 288 fitted thereover. At least one pressure sensor mat 288 may be disposed on each of the left and right platforms 22a, b. The pressure sensor mat 288 may be in electrical communication with the computer. The pressure sensor mats 288 may be operative to sense a pressure distribution of the underside surfaces of the user's feet and communicate the pressure distribution to the computer.

Figure 3:
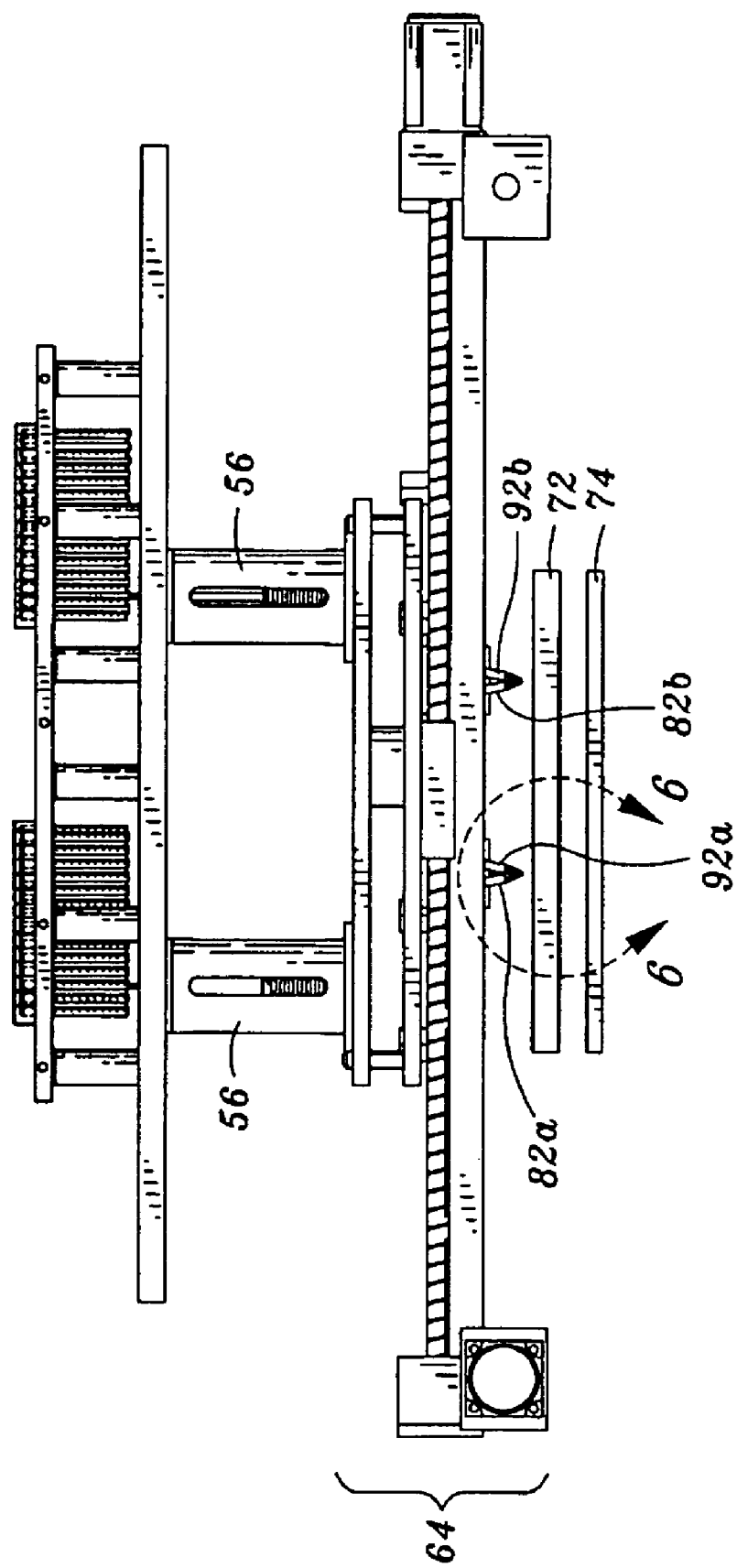
FIG. 3 is a front view of the measuring apparatus and the molding apparatus shown in FIG. 2 illustrating nozzles traverseably disposable over a cavity.

The studs 32 may be rotated via six (6) stepper motors 56 located on a base plate 58 (see FIGS. 2 and 21). The stepper motors 56 may be traverseably disposable under each of the studs 32. Three (3) of the stepper motors 56 may be disposed under the first set 30a of probes 28, and the other three (3) stepper motors 56 may be disposed under the second set 30b of probes 28, as shown in FIGS. 3 and 23. The stepper motors 56 may have hexagonal shaped distal tips 60 (see FIGS. 2 and 21) which are engageable to hexagonal shaped recesses formed on the lower distal ends 62 (see FIGS. 2A and 22A) of the studs 32. The stepper motors 56 may rotate the hexagonal shaped distal tips 60 in the clockwise as well as the counter clockwise direction to rotate the studs 32 into and out of the apertures 36 for raising and lowering the hex caps 34 or square caps 286 and altering the contours of the platforms 22a, b. The hexagonal shaped distal tips 60 of the stepper motors 56 may each have a tapered configuration. The tapered configuration allows the hexagonal shaped distal tips 60 to engage the hexagonal shaped recesses in the event that the tips 60 and recesses are out of angular alignment. The computer and the stepper motors 56 communicate with each other to determine amounts each of the probes 28 were vertically traversed.

In an aspect of the embodiment shown in FIG. 21, the middle stepper motors 56 disposed under the first and second sets of probes 28 may have a plurality of rotatable hexagonal shaped distal tips 60. Each of the middle stepper motors 56 is operative to rotate the plurality of hexagonal shaped distal tips 60. Preferably, each of the middle stepper motors 56 is operative to rotate four hexagonal shaped distal tips 60. Moreover, each of the plurality of hexagonal shaped distal tips 60 are engageable to a respective hexagonal shaped recess formed on the lower distal ends 62 of the studs 32 as discussed above.

It is also contemplated that the hexagonal shaped distal tips 60 may have other configurations such as triangular, octagonal, etc.

In operation, the distal tips 60 of the stepper motors 56 may be in a retracted position. The stepper motors 56 may be horizontally traversed under the studs 32 without the distal tips 60 of the stepper motors 56 interfering with the lower distal ends 62 of the studs 32. An X and Y motion control system 64 (see FIGS. 3 and 23), discussed in detail below, traverses the stepper motors 56 in the X and Y direction to align the distal tips 60 to the hexagonal shaped recesses of the studs 32. The stepper motor 56 traverses its distal tips 60 to an extended position. The distal tips 60 may be biased toward the extended position with a spring 66 (see FIGS. 2 and 21). As the distal tips 60 are traversed from the retracted position to the extended position, the distal tips 60 engage the hexagonal shaped recesses of the studs 32. If the distal tips 60 and recesses are not aligned, then the tapered configuration of the distal tips 60 rotates the distal tips 60 and the recesses into alignment such that the distal tips 60 may engage the recesses. The stepper motors 56 may rotate the stud 32 into or out of the aperture 36 to change the contour of the platforms 22a, b. Thereafter, the stepper motors 56 may traverse the distal tips 60 to the retracted position. The X and Y motion control system 64 may traverse the stepper motors 56 to adjust different probes 28. The traversal of the stepper motors 56 in the X and Y directions and the traversal of the distal tips 60 in the Z direction may take less than about ½ second per cycle. Accordingly, the adjustments for all of the probes 28 may take about one minute provided that the average number of probes to be adjusted for each foot is about three hundred (300) probes 28.

Figure 9:
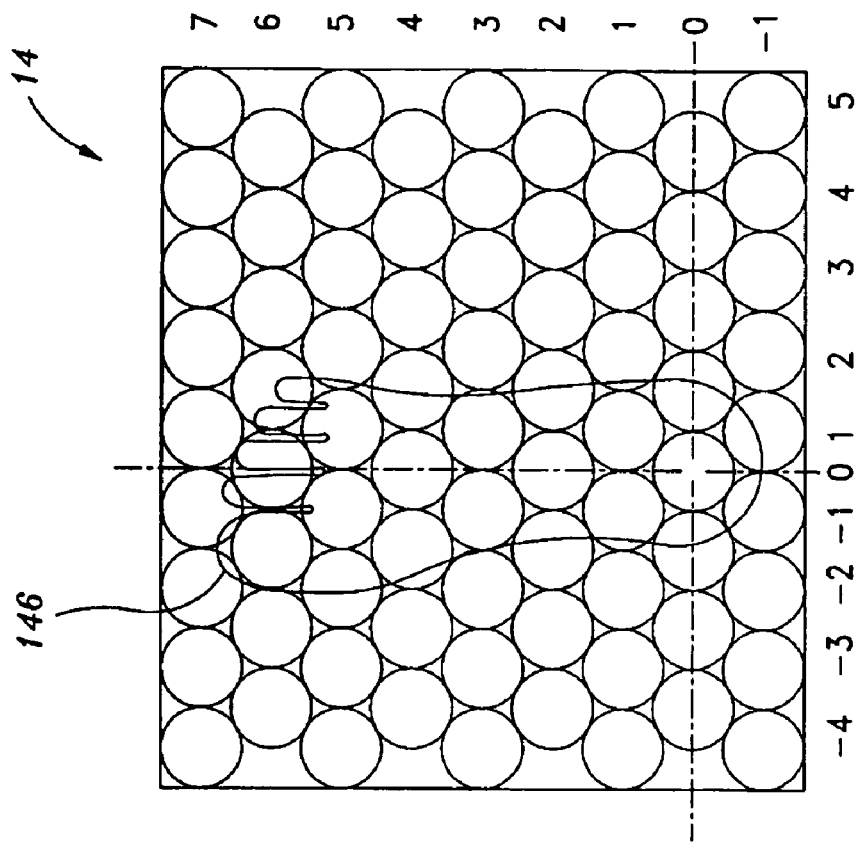
FIG. 9 is a foot display illustrating a mapped pressure distribution of an underside surface of a person's foot.

The user may step onto the left and right platforms 22a, b with his/her left foot and right foot, respectively. The hex caps 34 of the probes 28 may be vertically traversed until they are in a common plane (e.g., flat), and the pressure sensors 52 or pressure sensor mats 288 may sense pressures and communicate the sensed pressures to the computer. The computer may display the sensed pressures on the display 14 for the user to visualize the pressure distribution of his/her feet. An example of the display of the pressure distribution is shown in FIG. 9.

The display 14 may request the user to input the make, model and size of the purchased shoes or the shoes to be purchased. The computer may retrieve inner surface contours of the inputted shoes which may be the foot interface surfaces of the manufacturer's inserts (insoles) 20. The computer may also command the probes 28 to traverse vertically until the platforms 22a, b emulate the retrieved inner surface contours of the inputted shoes. This provides the user with an idea of how the shoes will feel without customized orthotics 12.

The pressure sensors 52 or pressure sensor mats 288 may sense the pressures on the underside surfaces of the user's feet and transmit such information to the computer. At this time, the computer may inform the user to remain still on the platforms 22a, b until the probes are again adjusted to redistribute the pressure on the underside surfaces of the person's feet optimally. This provides the user with a simulated feeling of customized orthotics 12 inserted into the purchased shoes. Moreover, the user is able to make a side by side comparison of the feeling of the shoe with and without the customized orthotics 12 to make an informed decision as to whether to purchase the customized orthotics 12. The user may switch between the two modes at a press of a button.

Figure 7A:
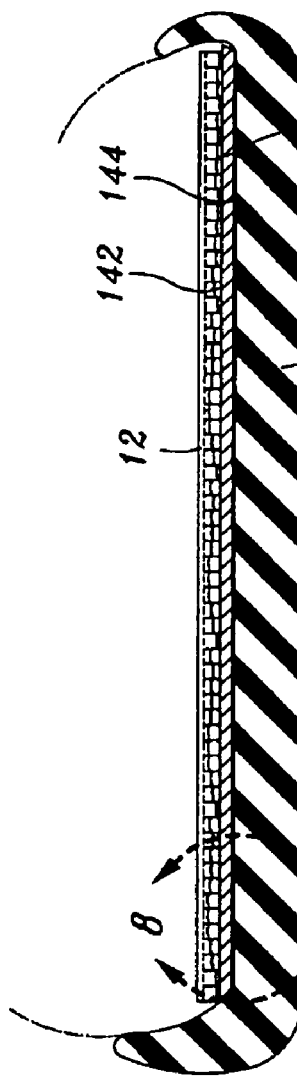
FIG. 7A is an illustration of an orthotic produced with the first version of the orthotic molding apparatus placed on top of a manufacturer's insole.
Figure 7B:
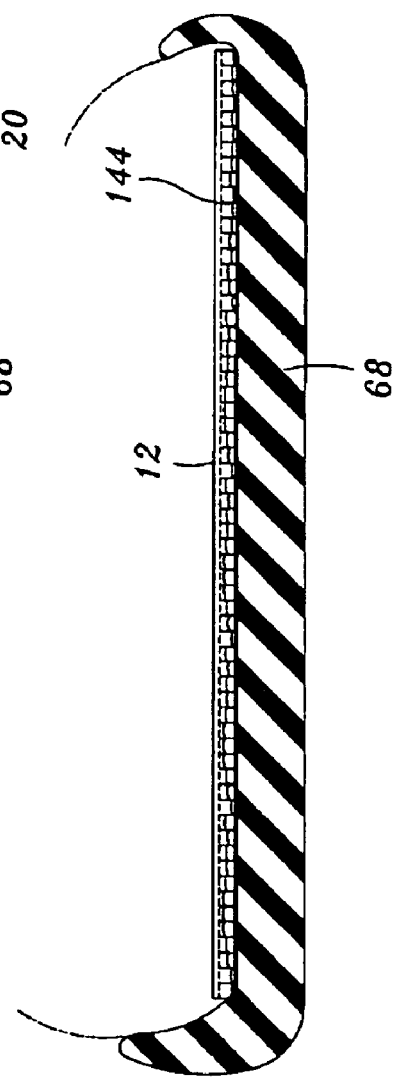
FIG. 7B is an illustration of an orthotic produced with the first version of the orthotic molding apparatus placed on top of a shoe's sole.
Figure 7C:
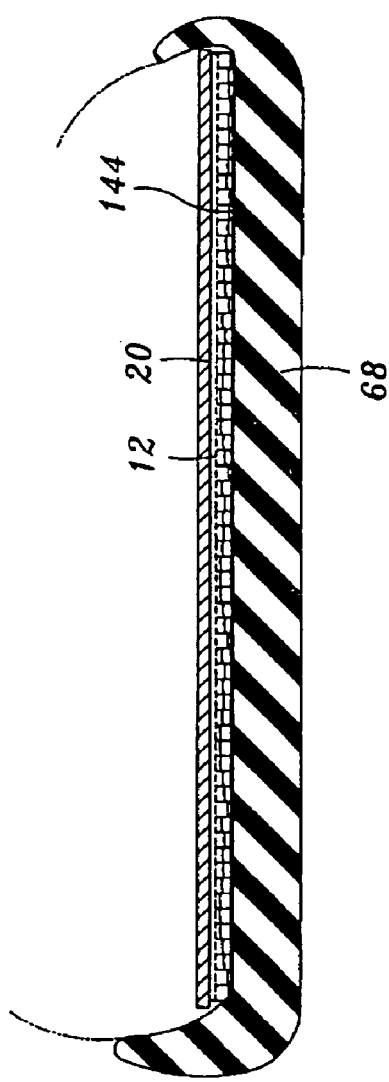
FIG. 7C is an illustration of an orthotic produced with the first version of the orthotic molding apparatus interposed between the shoe's sole and the manufacturer's insert.
Figure 18A:
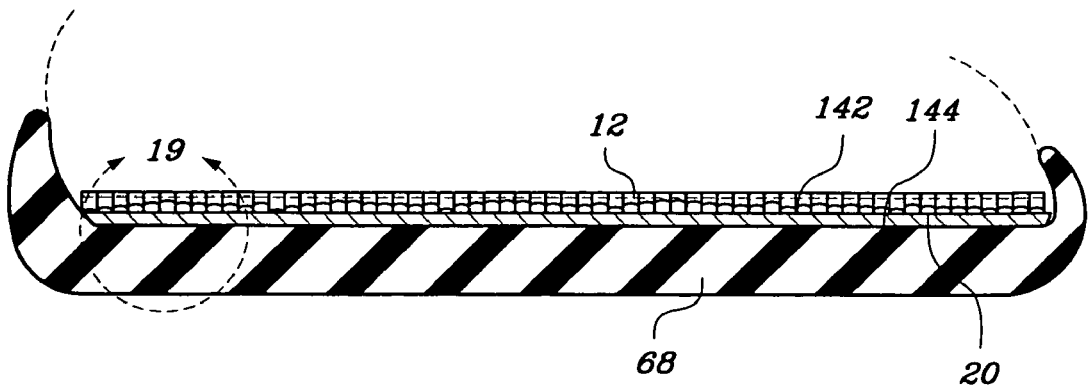
FIG. 18A is an illustration of an orthotic produced with the second version of the orthotic molding apparatus placed on top of a manufacturer's insole.
Figure 18B:
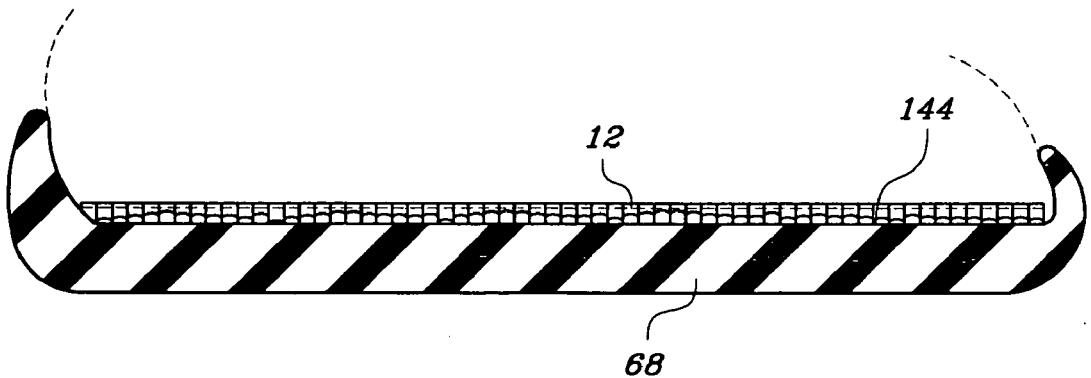
FIG. 18B is an illustration of an orthotic produced with the second version of the orthotic molding apparatus placed on top of a shoe's sole.
Figure 24A:
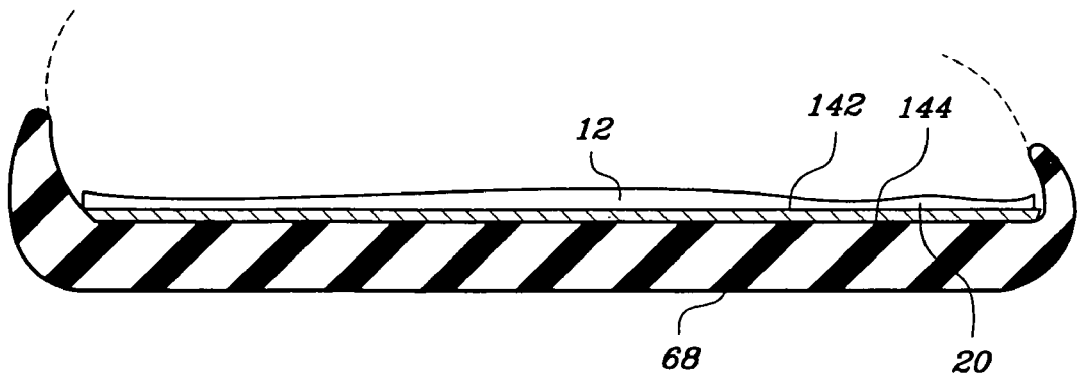
FIG. 24A is an illustration of an orthotic produced with the milling apparatus placed on top of a manufacturer's insole.
Figure 24B:
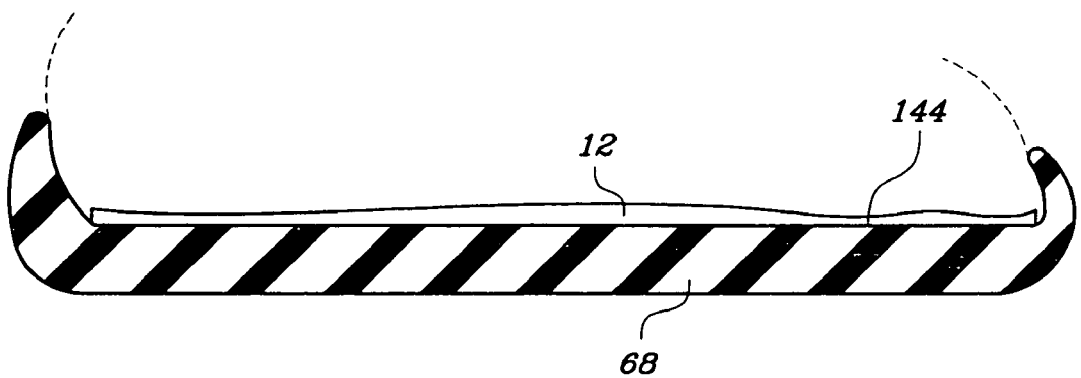
FIG. 24B is an illustration of an orthotic produced with the milling apparatus placed on top of a shoe's sole.
Figure 24C:
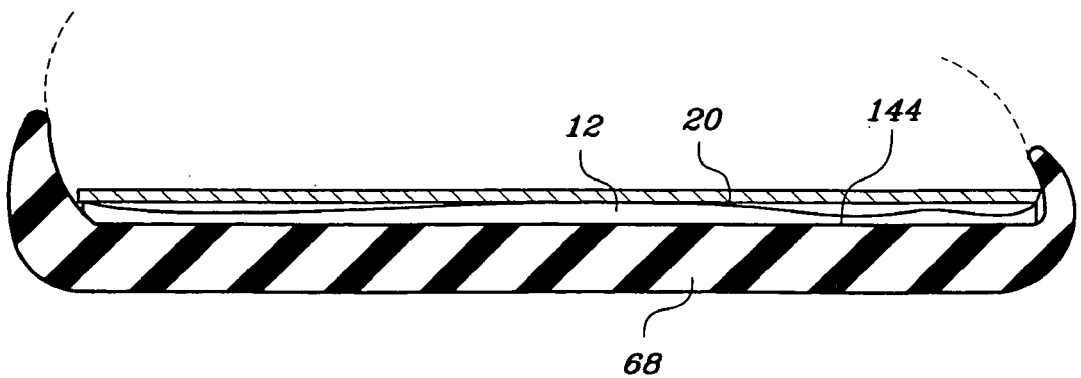
FIG. 24C is an illustration of an orthotic produced with the milling apparatus interposed between the shoe sole and the manufacturer's insert.

The user may purchase the customized orthotics 12 in three versions. In a first version, the customized orthotics 12 are placed on top of the manufacturer's inserts (insoles) 20, as shown in FIGS. 7A, 18A or 24A. In a second version, the customized orthotics 12 replace the manufacturer's shoe inserts (insoles) 20, as shown in FIGS. 7B, 18B or 24B. In this regard, the inner surface contours of the shoes are upper surfaces of the shoe's soles. In a third version, the customized orthotics 12 are interposed between the manufacturer's inserts (insoles) 20 and the shoe's soles 68, as shown in FIGS. 7B, 18B or 24B. During the adjustments of the probes 28 discussed above, heights of the probe's top surfaces 42 and pressures applied to the pressure sensors 52 may be recorded on a memory of the computer for subsequent processing. The computer may calculate a thickness and a hardness of the customized orthotics 12 based on the recorded heights and pressures. Additionally, the computer may calculate the thickness and hardness of the customized orthotics based on whether the customized orthotics 12 are placed on top of the manufacturer's inserts (insoles) 20, whether the customized orthotics 12 are interposed between the manufacturer's inserts (insoles) 20 and the shoe's soles 68, or whether the customized orthotics 12 replace the manufacturer's shoe inserts (insoles) 20.

After the computer calculates the thickness and hardness of the customized orthotics 12, the computer may then command the orthotic molding apparatus 18 (see FIGS. 2, 3 and 4; and FIGS. 11-17) or the orthotic milling apparatus 284 (see FIGS. 20 and 25) to fabricate the customized orthotics 12 in accordance with the calculated thickness and hardness.

Figure 4:
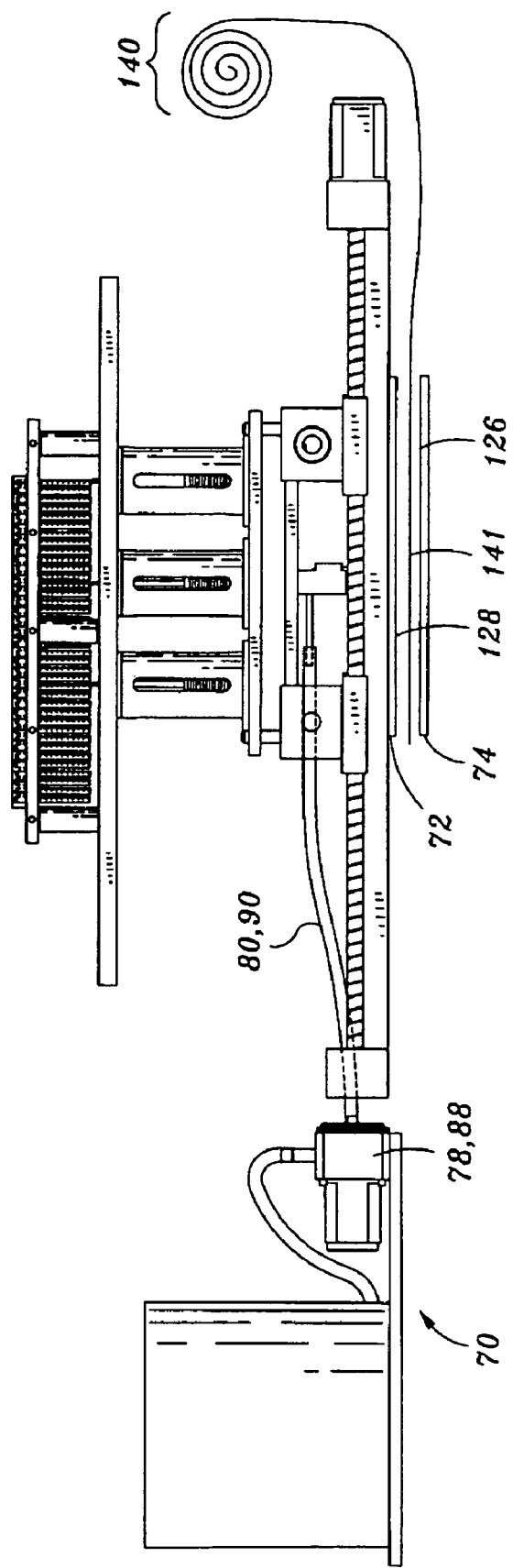
FIG. 4 is a side view of the measuring apparatus and the molding apparatus shown in FIG. 2.

In a first version of the orthotic molding apparatus 18, the same may comprise a polymerizable delivery system 70 (see FIGS. 2 and 4), a plurality of cavities 72 (see FIGS. 2 and 3), and a fabrication plate 74 (see FIG. 3). The customized orthotics 12 may be fabricated from a polymerizable material. By way of example and not limitation, the polymerizable material may be a two part silicon including a resin and a catalyst. It is also contemplated that other polymerizable materials that are heat, light, or UV cured may also be utilized such as but not limited to polyurethanes, certain other styrene, butyl and acrylic compounds The delivery system 70 may include a resin delivery sub-system and a catalyst delivery sub-system which respectively transfers resin and catalyst to cavities in a specific amount and specific ratio based on the calculated thickness and hardness. The resin sub-system may include a resin reservoir 76 (see FIG. 2) which may be filled with resin. The resin reservoir 76 may be in fluid communication with a left orthotic resin pump 78a and a right orthotic resin pump 78b, as shown in FIGS. 2 and 4. By way of example and not limitation, the pumps 78a, b may be a peristaltic pump. The left and right orthotic resin pumps 78a, b may be in fluid communication with left and right resin flexible tubes 80, respectively, as shown in FIG. 4. Moreover, the left and right resin flexible tubes 80 may be in fluid communication with left and right orthotic resin nozzles 82a, b, respectively, as shown in FIG. 3. The left orthotic resin nozzle 82a may be traversably disposable over each one of the cavities of a first set 84*a*, and the right orthotic resin nozzle 82*b* may be traversably disposable over each one of the cavities of a second set 84*b*.

Similarly, the catalyst delivery sub-system may include a catalyst reservoir 86 which may be filled with catalyst, as shown in FIG. 2. The catalyst reservoir 86 may be in fluid communication with a left orthotic catalyst pump 88*a* and a right orthotic catalyst pump 88*b*. By way of example and not limitation, the pumps 88*a, b* may be a peristaltic pump. The left and right orthotic catalyst pumps 88*a, b* may be in fluid communication with left and right catalyst flexible tubes 90 (see FIG. 4), respectively. Moreover, the left and right catalyst flexible tubes 90 may be in fluid communication with left and right orthotic catalyst nozzles 92*a, b*, respectively, as shown in FIG. 3. The left orthotic catalyst nozzle 92*a* may be traversably disposable over each one of the cavities of the first set 84*a*, and the right orthotic catalyst nozzle 92*b* may be traversably disposable over each one of the cavities of the second set 84*b*.

Moreover, the left orthotic resin nozzle 82*a* may be disposed immediately adjacent to the left orthotic catalyst nozzle 92*a* to sufficiently mix the resin and catalyst of the polymerizable material. The nozzles 82*a*, 92*a* may each have an output 94*a, b* (see FIG. 6) having an elongate thin configuration. For example, each output 94*a, b* may be about 0.030 inches long and about 0.010 inches wide. The outputs 94*a, b* may define centerlines 96*a, b* which intersect one another at an angle 100 of about 3 degrees to about 15 degrees, and preferable, at about 6 degrees. The nozzles 82*a*, 92*a* may be immediately adjacent to each other and centerlines 96*a, b* of the outputs 94*a, b* may intersect one another at an angle 100 such that the resin is effectively mixed with the catalyst when the resin and catalyst are injected into each of the cavities.

Likewise, the right orthotic resin nozzle 82*b* may be disposed immediately adjacent to the right orthotic catalyst nozzle 92*b* to sufficiently mix the resin and catalyst of the polymerizable material. The nozzles 82*b*, 92*b* may each have an output having an elongate thin configuration similar to the left orthotic resin and catalyst nozzles 82*a*, 92*a*. The nozzles 82*b*, 92*b* may be disposed immediately adjacent to each other and centerlines of the outputs may intersect one another at an angle such that the resin is effectively mixed with the catalyst similar to the left resin and catalyst nozzles 82*a*, 92*a*.

The left resin and catalyst nozzles 82*a*, 92*a* (see FIG. 3) are traverseably disposeable over each cavity of the left set 84*a* (see FIG. 2) of cavities. Also, the right resin and catalyst nozzles 82*b*, 92*b* (see FIG. 3) are traverseably disposable over each cavity of the right set 84*b* (see FIG. 2) of cavities. The nozzles 82*a*, 92*a* and 82*b*, 92*b* may be traversed over the cavities of the left and right sets 84*a* and 84*b* respectively, via the X and Y motion control system 64 (see FIG. 3). More particularly, the nozzles 82*a*, 92*a* and 82*b*, 92*b* may be connected to an underside of the base plate 58 (see FIG. 2). The base plate 58 may be mounted to a slideable block and a threaded block 102, as shown in FIG. 2. The threaded block 102 may be threaded onto a ball screw 104, and the slideable block may have an aperture (e.g., round, square, etc.) through which a corresponding bar 106 is slideably inserted. The ball screw 104 may be connected to a motor 108 which rotates the ball screw 104 and traverses the base plate 58 with the nozzles 82*a*, 92*a* and 82*b*, 92*b* in the X direction. The ball screw 104 and bar 106 may be mounted to a threaded block 110 and a slideable block 112. A ball screw 114 may be threaded onto the threaded block 110 and the slideable block 112 may have an aperture through which a corresponding bar 116 is slideably inserted. The ball screw 114 may be attached to a rotational motor 118 which rotates the ball screw 114 and traverses the base plate 58 with the nozzles 82*a*, 92*a* and 82*b*, 92*b* in the Y direction. In this manner, the nozzles 82*a*, 92*a* and 82*b*, 92*b* may be traversed in the X direction and the Y direction to position the nozzles 82*a*, 92*a* and 82*b*, 92*b* over any one of the cavities of the left and right sets 84*a* and 84*b*, respectively.

Each of the first and second sets 84*a*, 84*b* of cavities may have a honeycomb configuration, as shown in FIG. 5. In particular, the cavities 120 may be immediately adjacent to each other. Each cavity 120 may have six (6) cell walls 122 with each cell wall 122 shared by an adjacent cavity 120. Each cavity 120 may be about 0.43 inches in width 124 between opposing cell walls 122. The cell wall 122 may be about seventy-five (75) microns thick. Alternatively, the first and second sets 84*a, b* of cavities may be formed in a plate. The plate may be drilled with a plurality of apertures with each aperture having a diameter of about 0.43 inches.

The fabrication plate 74 may be disposed underneath the cavities 120, as shown in FIGS. 3 and 4. More particularly, as shown in FIG. 6, an upper surface 126 of the fabrication plate 74 may be disposed about 0.030 inches below the lower surface 128 of the cavities. For each of the cavities, the polymerizeable material may be disposed on the fabrication plate 74 and fill the cavity 120. A small portion of the injected material may be squeezed out under adjacent cavities 120 on the fabrication plate 74. The small portions squeezed out to adjacent cavities collectively form a layer 130 that spatially fixes the relationship between columnar pillars 132 of the material.

The nozzles 82*a*, 92*a* and 82*b*, 92*b* may be disposed above the cavities 120, as shown in FIG. 6. The pumps 78*a, b*, 88*a, b* may transfer a specific amount and ratio of resin and catalyst into each of the cavities 120 based on the calculated thickness and the calculated hardness of the customized orthotics 12. For example, as shown in FIG. 6, resin and catalyst may be injected into a first cavity 120*a*. Adjacent cavities 120*b*, 120*c* may have less resin and catalyst. Moreover, each of the cavities 120*a-c* may have a different ratio of resin and catalyst to make the columnar pillars 132 either harder or softer in accordance with the calculated thickness and calculated hardness of the customized orthotics 12. Additionally, the ratio of resin and catalyst injected into each of the cavities 120 may be varied vertically. For example, the material may be harder near the bottom 134 of the columnar pillars 132 and softer near the top 136 of the columnar pillars 132. The resin and catalyst not only fill in the cavity 120 but also fill in the space between the lower surface 128 of the cavities 120 and the upper surface 126 of the fabrication plate 74 thereby forming the layer 130 holding all of the columnar pillars 132 together. Moreover, the polymerizeable material may form a meniscus at an upper surface 138 of the columnar pillar 132. Preferably, the polymerizeable material wets the cell walls 122 such that the meniscus has a concave configuration. It is also contemplated that the meniscus may have a convex configuration.

As the polymerizeable material is polymerized, the material slightly shrinks thereby releasing itself from the sides of the cell wall 122, as shown in FIG. 6A. The cell wall sides may be coated with nickel Teflon to assist the material in releasing from the cell wall 122. After polymerization, the fabrication plate 74 may be lowered to remove the polymerized material from the plurality of cavities 120. The polymerized material may be removed from the plurality of cavities 120 by pushing the polymerized material out of the plurality of cavities 120. A knife may cut out the outer periphery of the polymerized material to form the left and right orthotics 12.

Additionally, a fabric or other material cover may be attached to the customized orthotics 12 to prevent the customized orthotics 12 from blistering the user's feet. For example, a roll 140 of nylon may be disposed adjacent to the fabrication plate 74, as shown in FIG. 4. The nylon fabric 141 may be interposed between the upper surface 126 of the fabrication plate 74 and the lower surface 128 of the cavities 120. The mixed resin and catalyst may be injected into the cavity 120 and disposed on the nylon fabric 141. The mixed resin and catalyst may attach to the nylon fabric 141 during the polymerizing stage. Additionally, cover materials may incorporate specifically designed time released bacteriocides and fungicides that are infiltrated into the fabric covers for control of foot odor and fungal control to prevent or minimize infectious conditions such as athletes foot.

Figure 8:
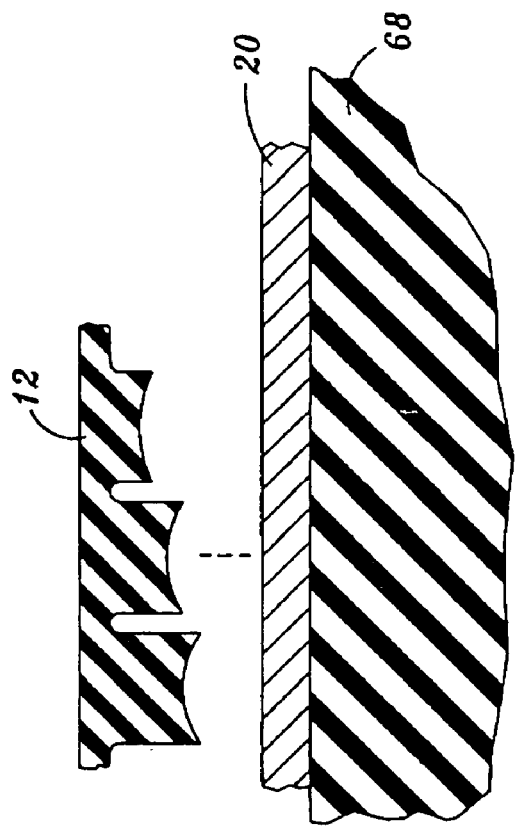
FIG. 8 is an enlarged view of FIG. 7A.

The user may place the left and right orthotics 12 on top of the manufacturer's shoe inserts (insoles) 20, as shown in FIGS. 7A and 8. Alternatively, the user may place the left and right orthotics 12 on top of the shoe's soles 68, as shown in FIG. 7B. More particularly, the meniscus side of the left and right orthotics 12 may interface with the upper surfaces 144 of the shoe's soles 68 (see FIG. 7B)) of the shoes. The concave shaped meniscus behaves as a suction cup attaching the orthotics 12 to the shoes' soles 68. Alternatively, the orthotics 12 may be interposed between the manufacturer's insert 20 and the shoe's sole 68 (see FIG. 7C). In all three placements, the orthotics were inverted.

In a second version of the orthotic molding apparatus 18, the same may include two separate orthotic manufacturing units 250. FIGS. 11-17 illustrate only one of the orthotic manufacturing units 250. A first orthotic manufacturing unit 250 may fabricate an orthotic for a left foot of a person. Also, a second orthotic manufacturing unit 250 may fabricate an orthotic for a right foot of a person. Alternatively, the orthotic manufacturing unit 250 shown in FIGS. 11-17 may have a honeycomb 252 sufficiently large with a sufficient number of apertures 254 to fit a left orthotic and a right orthotic. The orthotic manufacturing unit 250 may fabricate the orthotic by laying a plurality of discs 256 (see FIG. 12) on a base layer 258 (e.g., fabric, and the like; see FIGS. 11, 16, and 17) and permanently attaching the discs 256 to each other as well as to the base layer 258. The discs 256 may be selectively attached to the base layer 258 with respect to position, number of discs 256 and hardness.

Figure 11:
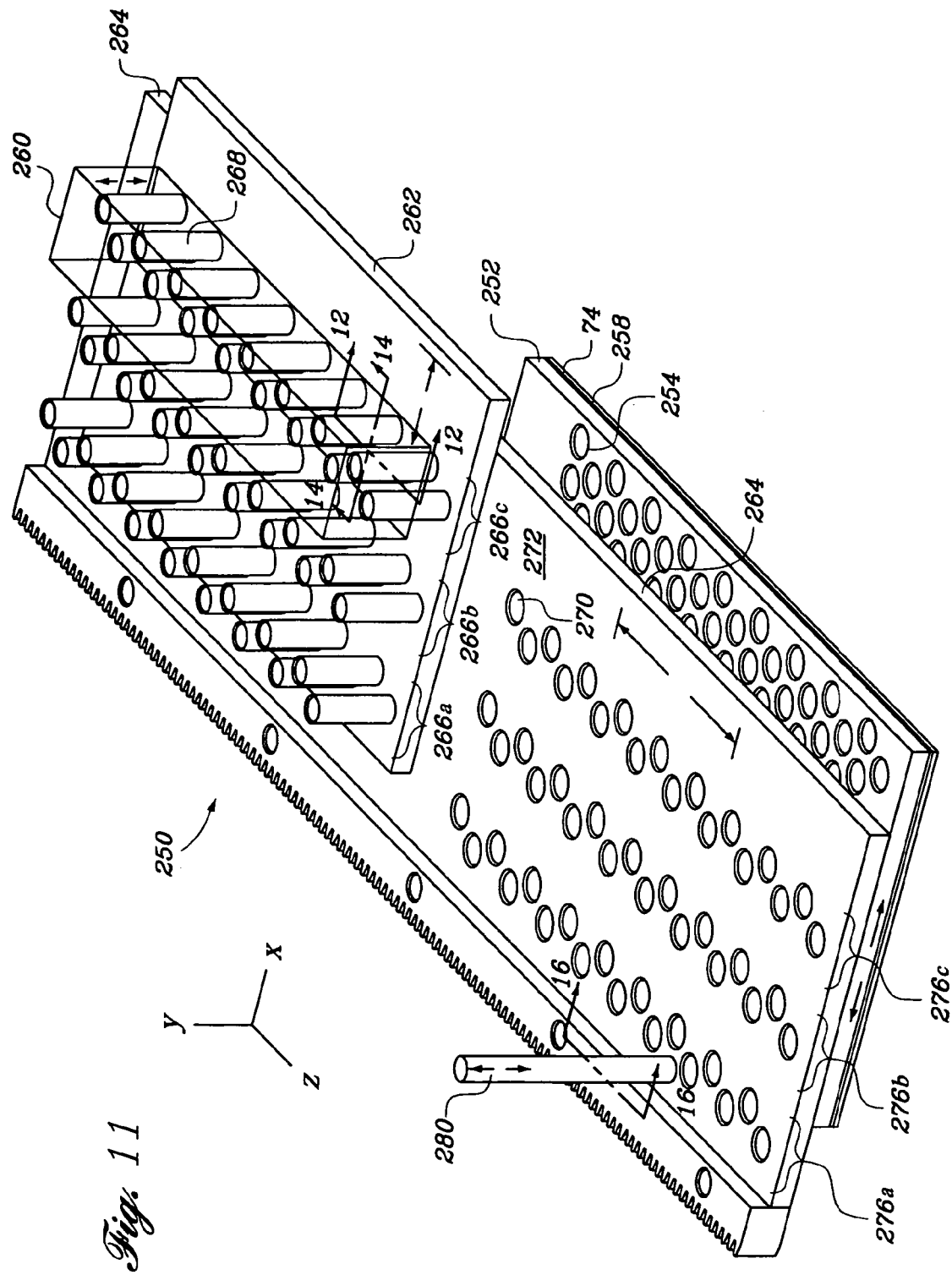
FIG. 11 is a perspective view of a second version of the orthotic molding apparatus.

Each of the orthotic manufacturing units 250 may have a hopper 260, tube plate 262, dispensing plate 264, honeycomb 252, the base layer 258 and the fabrication plate 74. The tube plate 262 may be fabricated with at least three rows 266a, b, c of a plurality of tubes. The tubes 268 of each row may be longitudinally stacked in an offset manner to increase the longitudinal density of the number of tubes 268 per row 266 of tubes, as shown in FIG. 11. Although FIG. 11 illustrates only one hopper 260 over a right row 266c of tubes, one hopper 260 may be placed over each row 266 of tubes 268. Each hopper 260 may contain a plurality of discs 256 having the same hardness. Also, the discs 256 in the different hoppers 260 may have a different hardness. For example, a left hopper 260 may contain a plurality of soft discs. A middle hopper 260 may contain a plurality of medium hardness discs. The right hopper 260 may contain a plurality of hard discs.

The hopper 260 may have four sidewalls which define an inner volume. The hopper 260 may have a top cover which is removably engageable to a top of the four sidewalls. A bottom of the hopper 260 may have a plurality of apertures which are sized and configured to receive a respective one of the tubes 268. The hopper 260 may be filled with discs 256 (see FIGS. 12 and 13) and the top cover placed on the hopper 260 to prevent any of the discs 256 from falling out of the hopper 260 during operation. The plurality of apertures formed on the bottom of the hopper may be sized and configured such that the discs 256 do not slip out of the hopper 260 between the tubes 268 and such apertures.

Figure 12:
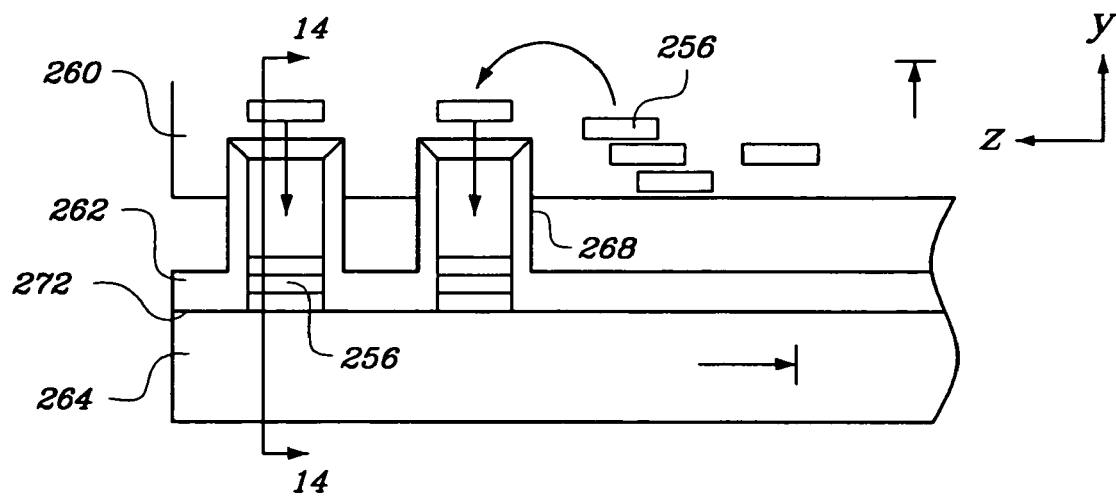
FIG. 12 is a cross sectional view of a hopper filled with discs traversed upward, a tube plate and a dispensing plate.
Figure 13:
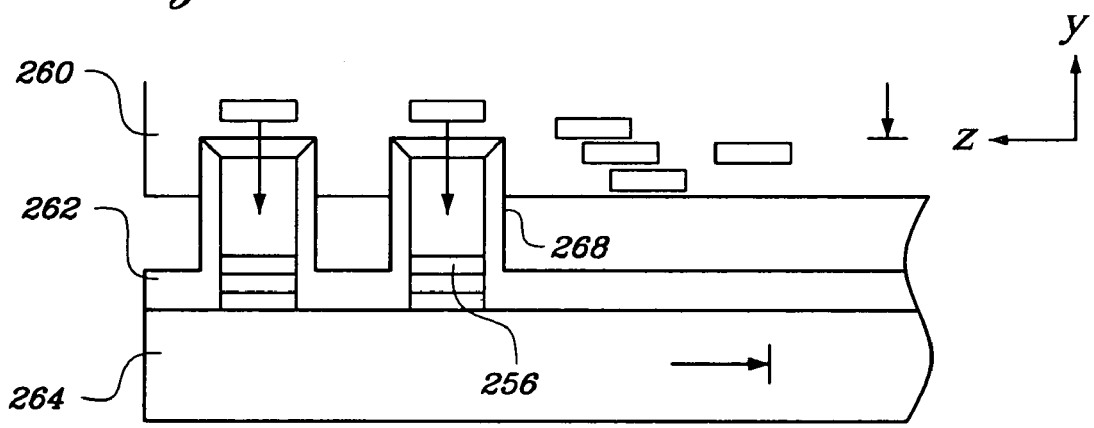
FIG. 13 is a cross sectional view of the hopper traversed downward which together with the upward movement shown in FIG. 12 fills tubes with the discs filled within the hopper.
Figure 14:
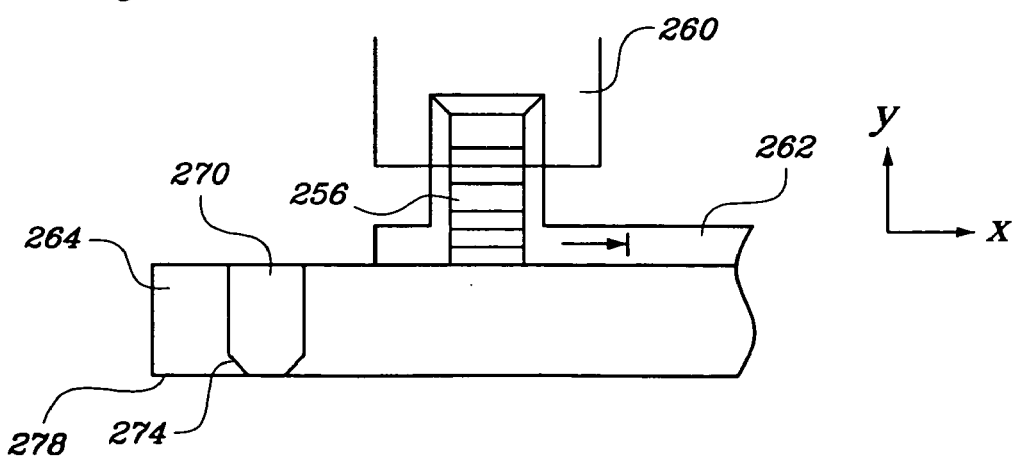
FIG. 14 is a cross sectional view of the tube plate and the dispensing plate wherein apertures of the dispensing plate are not aligned such that the discs are not filled in the tubes as the hopper is traversed upward as shown in FIG. 12 and downward as shown in FIG. 13.

With the hopper 260, tube plate 262 and dispensing plate 264 in the position shown in FIG. 11, the hopper 260 is rapidly traversed vertically in the plus and minus Y direction such that the tubes 268 are filled with the discs 256. As the hopper 260 is moved up (see FIG. 12) and down (see FIG. 13), the discs 256 within the hopper 260 begin to fill up each of the tubes 268, as shown in FIG. 12. When the tubes 268 are filled with discs 256, the hopper's vertical reciprocal movement is halted. At this point, the tubes 268 of each of the rows 266 of tubes have a plurality of discs 256 filled therein. A different hardness disc 256 may be filled in each of the row 266 of tubes. For example, a left row 266a of tubes 268 may be filled with soft discs, a middle row 266b of tubes 268 may be filled with medium hardness discs, and a right row 266c of tubes 268 may be filled with hard discs.

Figure 15:
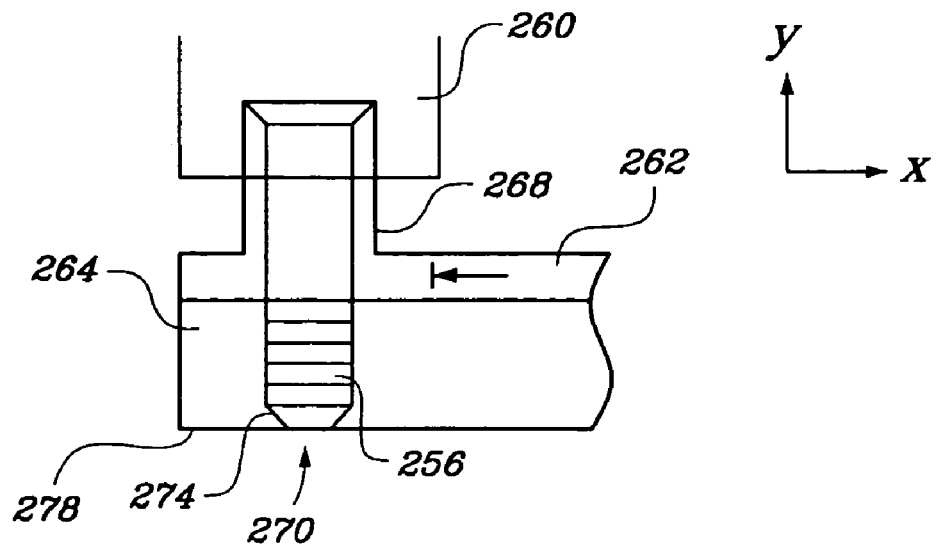
FIG. 15 is a cross sectional view of the tube plate and the dispensing plate wherein apertures of the dispensing plate are aligned such that discs are filled within the tubes of the tube plate for filling the apertures of the tube plate with discs.

The dispensing plate 264 is then traversed in the negative Z direction until apertures 270 of the dispensing plate 264 is aligned to the tubes 268 in the X direction. As the dispensing plate 264 is traversed in the negative Z direction, the discs 256 within the tubes 268 slide on a top surface 272 (see FIG. 12) of the dispensing plate 264. When the apertures 270 of the dispensing plate 264 are aligned to the tubes 268, the tube plate 262 is traversed in the negative X direction (see FIGS. 14 and 15) until the tubes 268 are vertically aligned to the apertures 270 of the dispensing plate 264, as shown in FIG. 15. At this point, the plurality of discs 256 within the tubes 268 slide down into the apertures 270 of the dispensing plate 264. A bottom edge of the apertures 270 of the dispensing plate 264 has an internal inwardly directed edge 274 (see FIGS. 14 and 15) which prevents the discs 256 from falling out of the apertures 270 of the dispensing plate 264. At this point, a left row 276a of apertures of the dispensing plate 264 may have soft discs, a middle row 276b of apertures of the dispensing plate 264 may have medium hardness discs, and a right row 276c of apertures of the dispensing plate 264 may have hard discs. The tube plate 262 is then traversed in the positive X direction and the dispensing plate 264 is traversed in the positive Z direction, as shown in FIG. 11.

Figure 16:
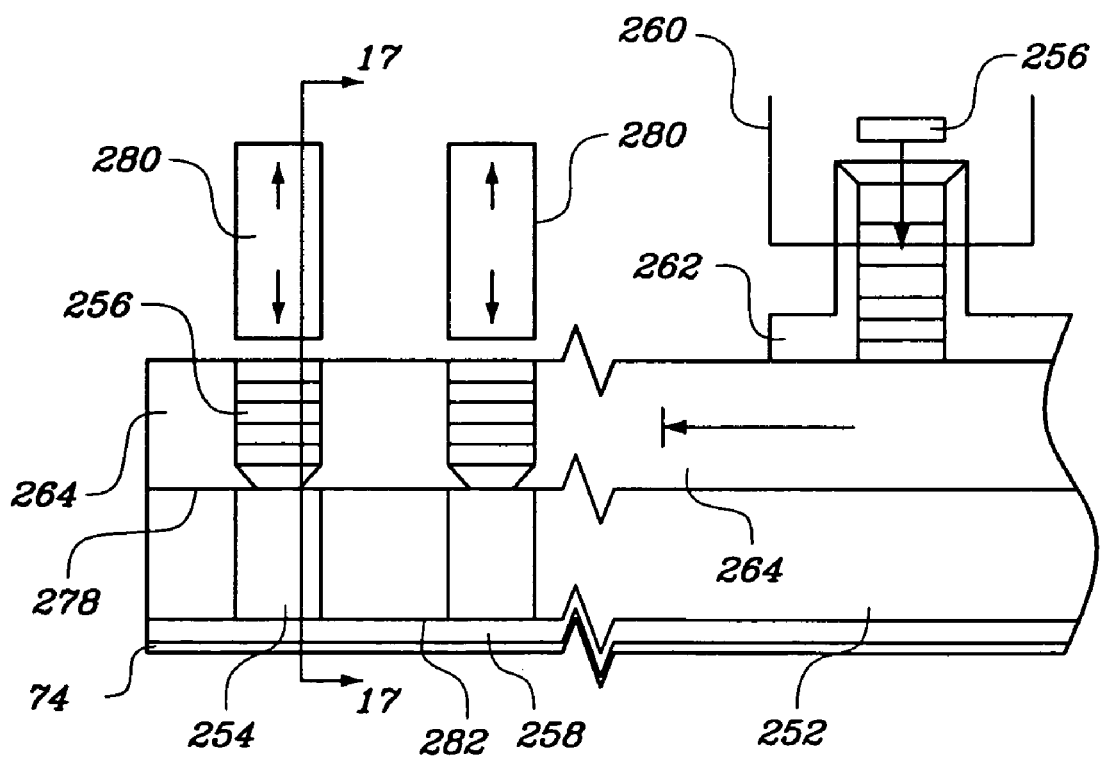
FIG. 16 is a cross sectional view of a pin, dispensing plate, base layer and fabrication plate, a selected numbers of discs being pushed into each aperture of the honeycomb.

The plurality of discs 256 are then displaced into the honeycomb 252 and on the base layer 258 by pushing the discs 256 through a bottom surface 278 of the dispensing plate 264 via pins 280, as shown in FIGS. 11 and 16. Once the discs 256 fall through the bottom surface 278 of the dispensing plate 264, the discs 256 are received into the aperture 254 of the honeycomb 252 and on the base layer 258, as shown in FIG. 17. The base layer 258 is disposed on the fabrication plate 74. The fabrication plate 74 and a bottom surface 282 (see FIGS. 16 and 17) of the honeycomb 252 do not have a gap as described in the first version of the orthotic molding apparatus 18. Rather, the base layer 258 contacts the bottom surface 282 of the honeycomb 252 such that the discs 256 are not permitted to move out of alignment with the aperture 254 of the honeycomb 252. The honeycomb 252 and base layer 258 are traversed in the positive and negative X direction. The pins 280 push a determined number of discs 256 of a determined hardness based on the measured height contour and pressure distribution previously performed into the apertures 254 of the honeycomb 252 until the apertures 254 of the honeycomb 252 are filled with the appropriate number of discs 256 and hardness.

Each of the apertures 254 of the honeycomb 252 may be filled with one or more discs 256 of the same or different hardness. As such, each of the apertures 254 of the honeycomb 252 may be filled with one or more soft discs 256, one or more medium hardness discs 256, one or more hard discs 256, or any combination thereof. By this manner, one aperture 254 of the honeycomb 252 may be filled with two different hardness discs 256 to fabricate a customized orthotic.

The orthotic vending machine determines the number of discs 256 and the hardness of the discs 256 to insert into each aperture 254 of the honeycomb 252 based on the height contour and pressure distribution of the underside surface of the person's foot. Also, the orthotic vending machine builds the orthotic based on the determined thickness and hardness with discs 256 via the method described herein.

In FIG. 11, although only one pin 280 is shown, a plurality of pins 280 may be positioned above the apertures 270 of the dispensing plate 264. Each of the pins 280 may push down the disc 256 within the dispensing plate 264 into the apertures 254 of the honeycomb 252. The pin 280 may be accurately vertically traversed via a servo motor such that the pin 280 may displace only a selected number of discs 256 into the apertures 254 of the honeycomb 252.

After the correct number of discs 256 of a particular hardness has been filled within the appropriate apertures 254 of the honeycomb 252, the discs 256 are permanently attached to each other as well as to the base layer 258. By way of example and not limitation, each side of the disc 256 may have an RF energy activated adhesive. After the correct number and type of discs 256 have been disposed within the apertures 254 of the honeycomb 252, the discs 256 and the base layer 258 may be exposed to RF energy which permanently attaches the discs 256 to each other and to the base layer 258. It is contemplated that any method of attaching the discs 256 to each other and to the base layer 258 may be used. A final cut in the shape of the inner periphery of the person's shoe is made to the base layer 258 and discs 256 such that the customized fabricated orthotic may be inserted in the person's shoe.

The discs 256 may have a flat circular shape. The discs 256 may be about 5 microns thick and about 9 mm in diameter. It is contemplated that any diameter and thickness disc may be used which is appropriate for the circumstance. The tubes 268 of the tube plate 262 may have a beveled entrance to permit the discs 256 to slide into the tubes 268 as the hopper 260 is being rapidly traversed up and down. The apertures 270 of the dispensing plate 264 may be sized and configured to receive the discs 256 from the tube plate 262. The apertures 270 of the dispensing plate 264 are shown as circular apertures; however, it is also contemplated that the apertures 270 of the dispensing plate 264 may have other configurations such as square, pentagonal, etc. so long as the discs 256 are receivable therein from the tube plate 262 and do not fall out through the bottom surface 278 of the dispensing plate 264. The apertures 254 of the honeycomb 252 are also shown as circular apertures; however, it is also contemplated that the apertures 254 of the honeycomb 252 may have other configurations such as square, pentagonal, etc. so long as the discs 256 are receivable therein from the dispensing plate 264 and maintains the discs 256 in a stacked configuration.

The base layer 258 discussed in relation to the second version of the orthotic molding apparatus 18 may have the same characteristics and treatment as the fabric discussed in relation to the first version of the orthotic molding apparatus 18.

Figure 18C:
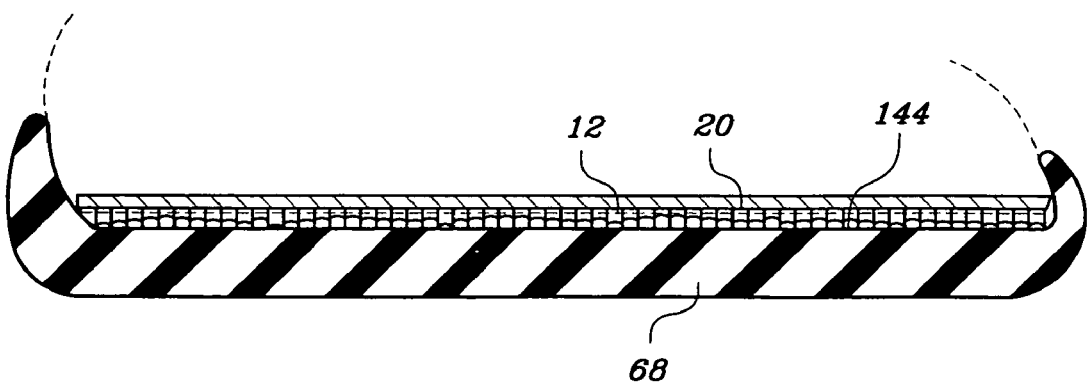
FIG. 18C is an illustration of an orthotic produced with the second version of the orthotic molding apparatus interposed between the shoe's sole and the manufacturer's insoles.

Referring now to FIGS. 18A-18C and 19, the user may place the left and right orthotics 12 fabricated by the second version of the orthotic molding apparatus on top of the manufacturer's shoe insoles 20 in a similar manner as shown in FIGS. 18A and 19. Alternatively, the user may place the left and right orthotics 12 on top of the shoe's soles 68 and discard the insoles 20, as shown in FIG. 18B. The disc side of the left and right orthotics 12 may interface with the shoe's soles 68. Alternatively, the orthotics 12 may be interposed between the manufacturer's insoles 20 and the shoe's sole 68 (see FIG. 18C). Similarly, the disc side of the left and right orthotics 12 may interface with the shoe's soles 68. As shown in FIGS. 18A-18C, the orthotics 12 are fabricated in an inverted manner.

Figure 25:
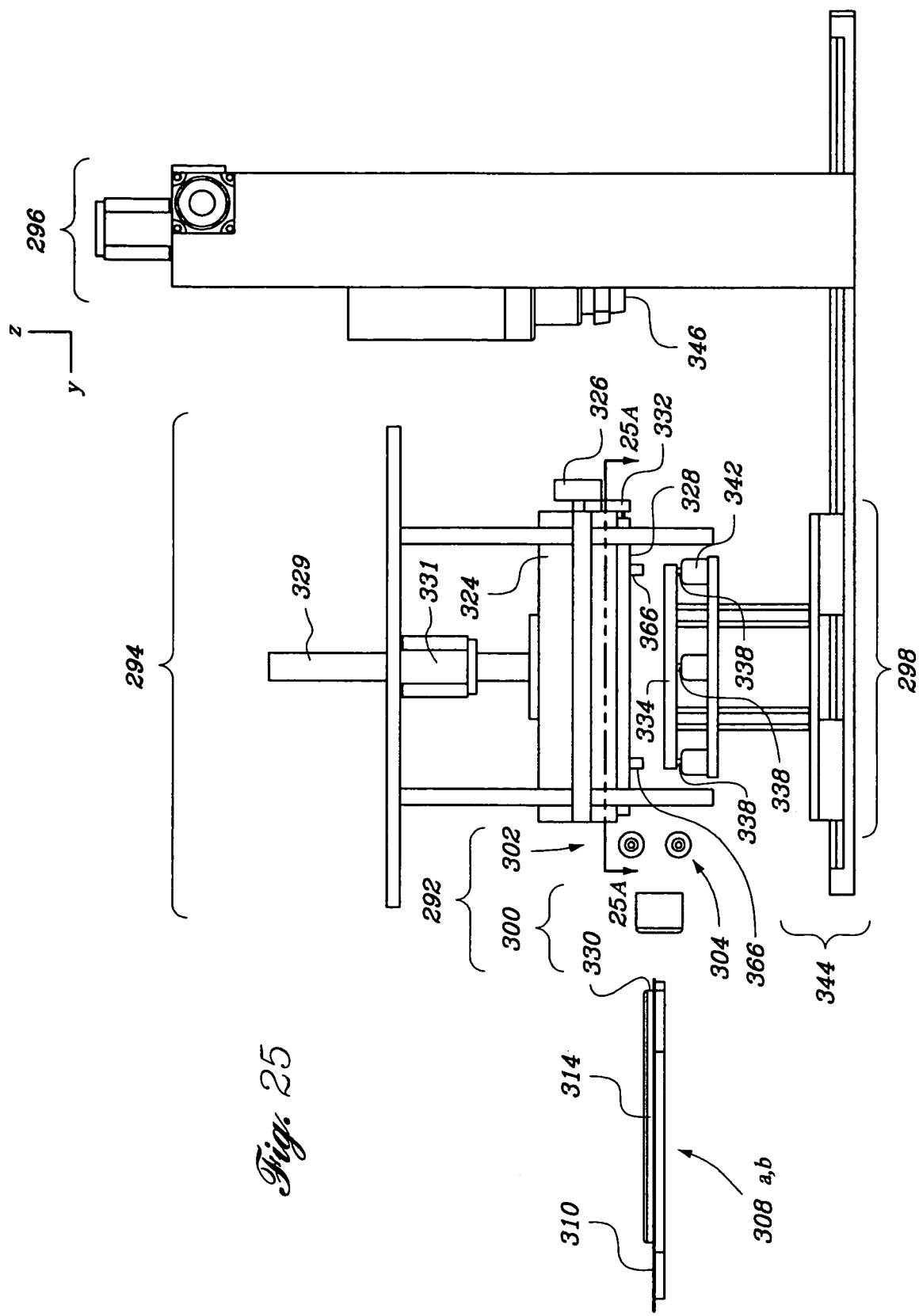
FIG. 25 is a side view of the milling apparatus shown in FIG. 20.

In relation to the milling apparatus 284, the same may comprise an entry section 292, laminator section 294, a milling section 296 and a machining platform 298, as shown in FIGS. 20 and 25.

The entry section 292 may comprise an entry port 300 and a pair of upper and lower grippers 302, 304. The entry port 300 may have an aperture 306 (see FIG. 20) sized and configured to receive a near net shaped orthotic left and right blanks 308a, b (see FIGS. 20, 25, and 26) and a cover layer 310 (see FIGS. 20 and 25) disposed on top of the near net shaped orthotic left and right blanks 308a, b. More particularly, the aperture 306 of the entry port 300 may have an elongate opening with a center railway 312 (see FIG. 20) formed at an upper side of the entry port 300 opening. The center railway 312 may be sized and configured to receive a rail 314 of the orthotic blanks 308. As shown in FIG. 26, the orthotic blanks 308 may be provided as near net shaped orthotic left and right blanks 308a, b. The left orthotic blank 308a and the right orthotic blank 308b may be connected to each other with a set of webs 316. The rail 314 protrudes upwardly above the top surfaces 318 of the left and right orthotic blanks 308a, b and may have a straight elongate configuration. When the rail 314 of the orthotic blanks 308a, b is received into the center railway 312 (see FIG. 20) of the entry port 300, the left and right orthotic blanks 308a, b are registered or aligned in the X direction. The user continues to push the cover layer 310 and the near net shaped orthotic blank 308 through the entry port 300. When a leading edge 320 (see FIG. 26) of the orthotic blank 308 contacts the upper and lower grippers 302, 304, the upper and lower grippers 302, 304 traverse the cover layer 310 along with left and right orthotic blanks 308a, b toward the laminator section 294. When the upper and lower grippers 302, 304 grip the orthotic blank 308, the rail 314 of the orthotic blank 308 is also received into a groove 322 (see FIG. 20) formed in the upper gripper 302. As such, the center railway 312 and the groove 322 of the upper gripper 302 registers the orthotic blank 308 in the X direction with respect to the milling apparatus 284.

Figure 27:
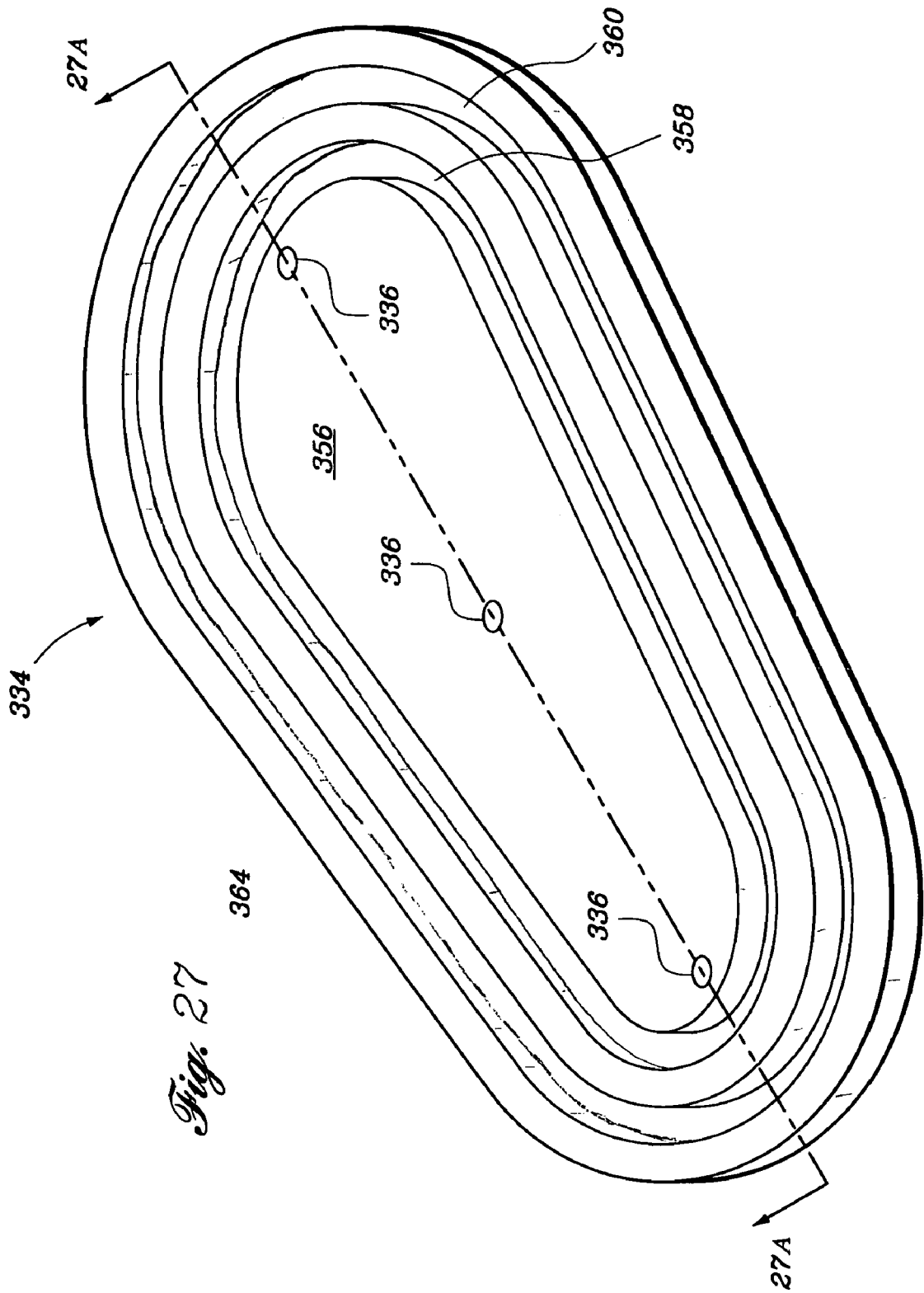
FIG. 27 is a top perspective view of a machining platen of the milling apparatus.

As shown in FIG. 25, the laminator section 294 may include a heating block 324, heating element 326 and a heatable/compressable gel 328 which are collectively traversable between a retracted position, a receiving position and an extended position via a screw 329 and motor 331. In the receiving position, the rail 314 of the orthotic blank 308 is receivable into an optional straight groove 354 (see FIG. 25A) formed on the underside of the laminator 294. The groove 354 may be formed by left and right gels 328 or machined in a lower surface of the heating block 324. As the upper and lower grippers 302, 304 traverse the orthotic blank 308 further into the laminator section 294, the rail 314 slides in the straight groove 354 formed on the underside of the laminator 294. The upper and lower grippers 302, 304 traverse the orthotic blank 308 into the laminator section 294 at a sufficient speed such that a leading edge 330 of the rail 314 is thrusted up against a limit switch 332 located at a front portion of the heating block 324. When the rail 314 contacts the limit switch 332, the rollers 302, 304 may stop rotating. Additionally, this registers or aligns the orthotic blank 308 in the Y direction with respect to the milling apparatus 284. The left orthotic blank 308a and the right orthotic blank 308b may rest on a pair of machining platens 334 (see FIGS. 25, 27 and 27A) when the left and right othonic blanks 30a, b are aligned in the laminator section 294. A top perspective view of one of the left and right machining platens 334 is shown in FIG. 27. At this point, the orthotic blanks 308 are registered or aligned with respect to the X and Y axes with respect to the milling apparatus 284. The machining platen 334 may have three apertures 336 which are sized and configured to slidingly receive threaded bolts 338 (see FIGS. 25 and 27A). Threaded bolts 338 (see FIGS. 25 and 27A) may be traversed upward through machining platen holes 336 and rotated so as to be received into respective threaded holes 340 (see FIG. 26 and 27A) in the orthotic blanks 308. The threaded bolts 338 engage the threaded holes 340 of the orthotic blanks 308 and secure the orthotic blanks 308 to the machining platens 334. The bolts 338 are vertically traversable and rotatable via the motors 342 disposed beneath the machining platens 334.

After the orthotic blanks 308a, b are secured to the machining platens 334, the laminator 294 may have a plurality of pins 366 (see FIGS. 25 and 25A) which are received into corresponding holes 368 (see FIG. 26) of the cover layer 310 so as to grab or lift the cover layer 310 off of the orthotic blank 308 and temporarily hold the cover layer 310 to an underside of the heatable/compressable gels 328, as will be explained further below. The laminator 294 along with the cover layer 310 is traversed upward to a retracted position. In the retracted position, the rail 314 of the orthotic blanks 308 and the limit switch 332 of the laminator 294 do not interfere with each other. The machining platens 334 may then be traversed toward the milling section 296 via a Y direction motion control system 344 (see FIG. 25). Once the orthotic blanks 308 are disposed under the milling section 296, a milling head 346 mills out upper surfaces of the orthotic blanks 308 according to the measured pressure distribution of the underside surfaces of the user's feet. The Y direction motion control system 344 controls the orthotic blanks 308 in the Y direction, whereas, the milling section 296 has an X-Z motion control system 348 (see FIG. 20) to position the milling head 346 to the orthotic blanks 308 in the X-Y directions.

After the orthotic blanks 308 are milled via the milling section 296, the milled blank is traversed into the laminator section 294. The laminator 294 is traversed to an extended position wherein the cover layer 310 is pressed on top of the milled orthotic blank 308. A lower surface of the cover layer 310 may have a heat activated pressure adhesive (e.g., permanent adhesive or peelable adhesive such that cover layer 310 may be removed from the milled blanks for washing). While the orthotic blanks 308 were being milled out via the milling section 296, the heating element 326 may have been activated so as to heat the heating block 324 and the heatable/compressable gels 328 thereby activating the adhesive of the cover layer 310. Accordingly, when the laminator 294 is traversed to the extended position, the heat activated adhesive of the cover layer 310 is activated such that the cover layer 310 is now adhered or attached to the top surfaces 318 of the milled blanks 308. At the extended position, the gels 328 press the cover layer 310 onto the top surfaces 318 of the milled blanks 308. Since the gels 328 are compressable or formable, the gels 328 provide an even pressure onto the orthotic blanks 308. After a sufficient period of time to adhere the cover layer 310 to the orthotic blank 308 has elapsed, the laminator 294 is traversed to the retracted position and the pins 366 of the laminator 294 release the holes 368 of the cover layer 310. The orthotic blank 308 and the adhered cover layer 310 is traversed back toward the milling section 296 wherein the milling head 346 trims excess cover layer 310 which overhangs the orthotic blank 308. Thereafter, the machining platen 334 is traversed back under the laminator section 294. The bolts 338 of the machining platen 334 are disengaged from the threaded holes 340 of the orthotic blanks 308. The machining platen 334 is then traversed rearward until the upper and lower grippers 302, 304 grip trailing edges 350 (see FIG. 26) of the milled orthotics. The milled orthotics are pulled through the entry port and delivered to the end user.

In an aspect of the milling apparatus 284, the waste particulate due to the milling operation may be cleared from the milling apparatus 284 via compressed air blown toward the direction of the milling head 346, a brush and a belt system.

In another aspect, FIG. 26 is a perspective view of the near net shaped left and right orthotic blanks 308a, b. As shown, the left orthotic blank 308a and the right orthotic blank 308b may be connected to each other via a system of webs 316. In each of the left and right orthotic blanks 308a, b, three threaded holes 340 may be formed through each of the left and right orthotic blanks 308a, b. These threaded holes 340 may be aligned and sized and configured to mate with the threaded bolts 338 (see FIGS. 25 and 27A) which are vertically traversable through the machining platen 334 and engageable with the threaded holes 340. The rail 314 extends above the top surfaces 318 of the left and right orthotic blanks 308a, b and may be centrally formed between the left and right orthotic blanks 308a, b. The rail 314 may have a straight elongate configuration. The rail 314 may also be sized and configured to be received into the center railway 312 (see FIG. 20) of the entry port 300, the groove 322 (see FIG. 20) of the upper gripper 302 and the straight groove 354 (see FIG. 25A) of the laminator 294.

The top surfaces 318 of the left and right orthotic blanks 208a, b may have a contoured shape sized and configured to the general shape of the underside contour of predetermined feet. Additionally, the lower surface of the left and right orthotic blanks 308a, b may have grooves and other prefabricated contours. The grooves and prefabricated contours of the upper and lower surfaces of the left and right orthotic blanks 308a, b permit the milling head 346 to merely fine tune (i.e., mill off a minimal amount of material) the left and right orthotic blanks 308a, b to the particular contours of the user's feet. For example, a plurality of different types of left and right orthotic blanks 308 may be provided with the orthotic vending machine 10. Each of the orthotic blanks 308 may have different upper and lower contoured surfaces designed to meet the needs of the user's feet. One orthotic blank 308 may be sized and configured to the general underside contours of a person who is flatfooted with small feet. Another orthotic blank 308 may be sized and configured to users with small feet but specially contoured to alleviate pronating feet. When the milling section mills the orthotic blanks, the milling head does not have to mill off gross amounts of material but merely needs to fine tune the particular orthotic blanks to the user.

In an aspect of the milling apparatus 284, as stated above, the orthotic blanks 308 and the cover layer 310 are thrusted into the laminator section 294 at a sufficient high speed such that a leading edge 330 of the rail 314 bumps up against the limit switch 332. Alternatively, as shown in FIG. 25A, the heating blocks 324 may have left and right rollers 352a, b. The left and right rollers 352a, b may grasp the rail 314 of the orthothic blanks 308 when the rail 314 of the orthotic blanks 308 is disposed within the groove 354 formed on the underside surface of the heating block 324. Instead of thrusting the orthotic blanks 308 and the cover layer 310 into the laminator section 294, the rollers 352a, b may rotate in conjunction with each other to traverse the rail 314 and orthotic blanks 308 in a forward motion. When the leading edge 320 of the rail 314 contacts the limit switch 332, the limit switch 332 may send a signal to stop rotation of the rollers 352a, b. At this point, the orthotic blanks 308 are aligned in the X and Y directions.

In an aspect of the milling apparatus 284, the orthotic blanks 308 may be provided in a plurality of different sizes. Preferably, the orthotic blanks 308 are provided in a small size 308f, medium size 308e, and a large size 308d, as shown in FIG. 27A. Within each of the sizes, the orthotic blanks 308 may be sized and configured to the general shape of the underside surfaces of predetermined feet and also to correct various foot conditions (e.g., a supination, pronation, etc.). FIG. 27A illustrates three different sized orthotic blanks 308d, e, f wherein the leading edge 330 of the rail 314 of the orthotic blanks 308 is aligned in the Y direction. FIG. 27A does not illustrate three orthotic blanks 308 simultaneously disposed between the laminator section 294 and the machining platen 298. Rather, it merely illustrates the position of one of the orthotic blanks 380d, e, f in the Y direction when the rail 314 is received into the groove 354 (see FIG. 25A) of the laminator and the leading edge 330 of the rail 314 contacts the limit switch 332. As can be seen in FIG. 27A, the bolts 338 are not aligned to the holes 340 of the orthotic blanks 308d, e, f when they 308 are aligned in the Y direction. Accordingly, the machining platen 334 may be traversed in the Y direction to align the bolts 338 to the respective holes 340 of the respective orthotic blanks 380d, e, f. After the bolts 338 are aligned to the holes 340, the bolts may be traversed upwardly through holes 336 and screwed onto the threaded holes 340 to secure the orthotic blank 380 to the machining platen 334.

Referring to FIGS. 27 and 27A, the machining platen 334 may have an upper surface 356 with an inner groove 358 and an outer groove 360. The upper surface 356 supports the orthotic blanks 308 when the orthotic blanks 308 are secured to the machining platen 334. For small sized orthotic blanks 308f, an outer periphery 362 (see FIG. 26) is aligned to the inner groove 358. For medium sized orthotic blanks 308e, an outer periphery 362 thereof is aligned to the outer groove 360. For large sized orthotic blanks 308d, an outer periphery 362 thereof overhangs the outer periphery 364 of the machining platen 334 (see FIG. 27). When the milling head 346 mills out the outer periphery 362 of the milled orthotic 308 or the excess cover layer 310, the milling head 346 may be received into the inner groove 358, outer groove 360 or outside the boundary of the outer periphery 364 of the machining platen 334.

After the orthotic blanks 308 have been milled by the milling section 296, the trailing edge 350 of the medium sized orthotics 308e and the small sized orthotics 308f do not overhang the machining platen 334. As such, the upper and lower grippers 302, 304 may not grasp the trailing edge 350 to pull the milled orthotics 308 out of the laminator section 294 and deliver the same to the user. Instead, after the machining platen 334 is traversed under the laminator section 294, the laminator 294 is then traversed to the receiving position. At this point, the rail 314 may now disposed between the rollers 352a, b (see FIG. 25A) of the laminator section 294. Now, the rollers 352a, b may grasp the rail 314 and traverse the milled orthotic 308 back into the upper and lower grippers 302, 304.

Figure 28:
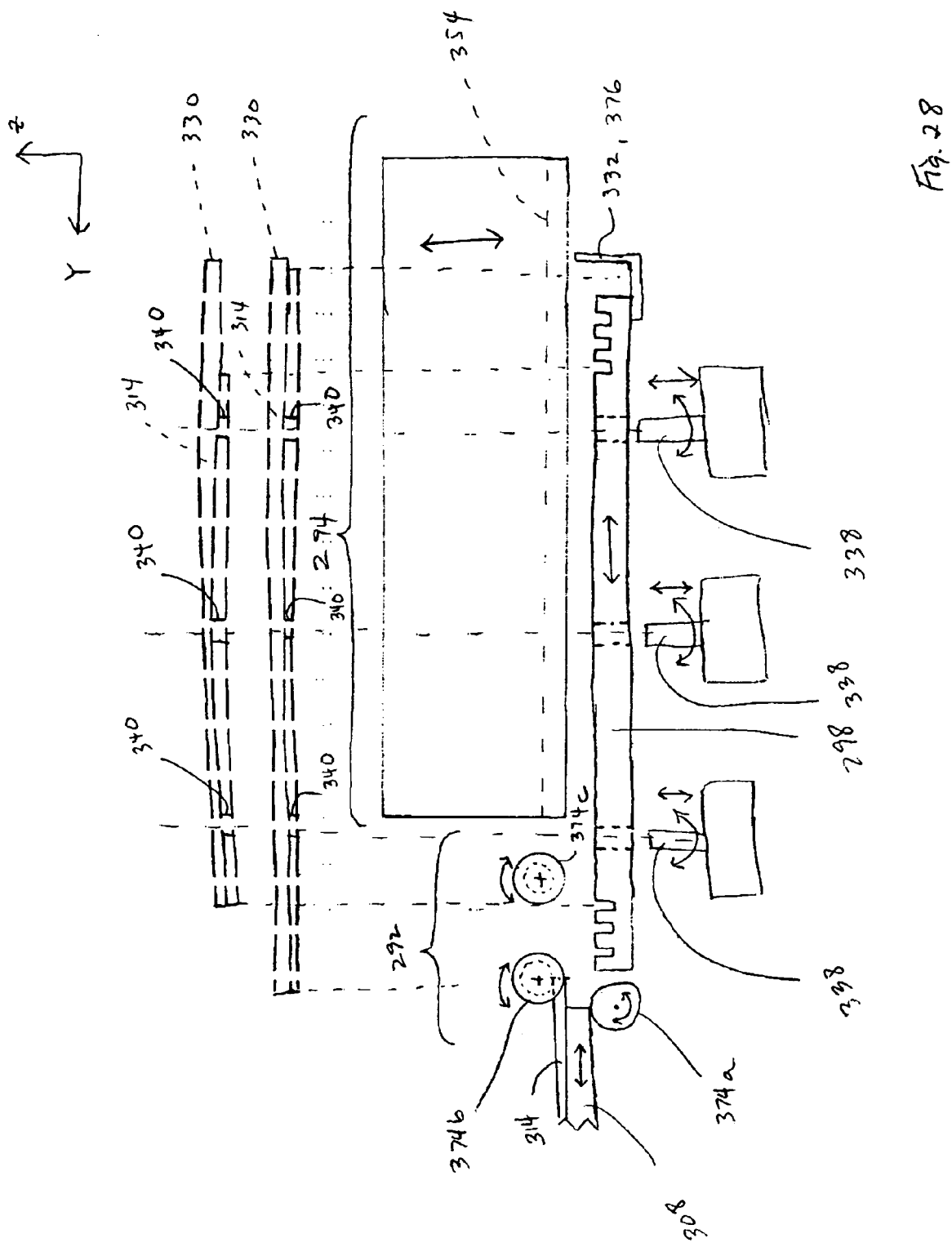
FIG. 28 is an alternative entry section compared to the entry section of FIG. 20 and an alternative to the blanks shown in FIG. 27A.

FIGS. 28 and 29 illustrate an alternate embodiment of the entry section 292 and orthotic blanks 308 compared to the entry section 292 shown in FIG. 20 and the orthotic blanks 308 shown in FIG. 27A. The entry section 292 shown in FIG. 28 may have a plurality of rollers 374a, b, c to traverse the orthotic blanks 308 (see FIG. 29) into and out of the laminator section 294. In particular, the entry section 292 may have an idle roller 374a positioned underneath the orthotic blanks 308. A first upper roller 374b may be vertically offset from the idle roller 374a. The first upper roller 374b may be rotateable in the counter clockwise direction to traverse the blanks 308 into the laminator section 294 or clockwise to traverse the blanks 308 out of the laminator section 294. The first upper roller 374b may also be spring loaded to apply pressure onto the blanks 308 as the blanks 308 are being traversed into and out of the laminator section 294.

In operation, the blank 308 is grasped by the first upper roller 374b and the idle roller 374a. The blank 308 is traversed forward until the leading edge 330 of the rail 314 contacts the limit switch 332 or mechanical stop 376 attached to the front portion of the machining platform 298. The limit switch 332 may send an electrical signal to the rollers 374b, c to stop rotating. At this point, the rollers 374a, b, c stop traversing the blank 308 into the laminator section 294 and the blanks 308 are aligned in the Y direction to the machining platform 298 such that the threaded bolts 338 are aligned to the threaded holes 340 of the blanks 308. The mating grooves 354 and rail 314 align the blanks 308 in the X direction. The threaded bolts 338 engage threaded holes 340 and the milling apparatus 284 may operate as discussed herein.

FIG. 29 illustrates two different sized blanks 308—large and small orthotic blanks 308. Other sizes are also contemplated and employable with the milling apparatus 284 discussed herein. The operation of the idle roller 374a in conjunction with the first upper roller 374b may be sufficient to traverse the large blanks into the laminator section 294 or the rail 314 up against the limit switch 332 or mechanical stop 376. However, for small orthotic blanks 308, as shown on the right hand side of FIG. 29, the idle roller 374a and the first upper roller 374b may release the small orthotic blanks 308 before the leading edge 330 of the rail 314 contacts the limit switch 332 or mechanical stop 376. In this instance, the second upper roller 374c, which is operative to rotate counter clockwise and clockwise and is spring loaded, may push the small orthotic blanks 308 against the machining platen 298 and push the small orthotic blanks 308 forward until the leading edge 330 of the rail 314 contacts the limit switch 332 or mechanical stop 376. If the limit switch 332 is employed, the limit switch 332 may send an electrical signal to the rollers 374a, b, c to stop rotating. The threaded holes 340 of the blanks 308 are aligned to the threaded bolts 338. The threaded bolts 338 may be engaged to the threaded holes 340 and the orthotic blanks 308 milled via the milling section 296, as discussed herein.

When the milled orthotic blanks 308 are ready to be ejected out of the vending machine or presented to the customer, the threaded bolts 338 disengage the threaded holes 340 and the first and second upper rollers 374b, c are rotated in the clockwise direction to eject the milled orthotic 308 out of the vending machine.

The orthotic blanks 308 shown in FIG. 29 may be formed such that the threaded holes 340 are always in the same position when loaded onto the machining platform 298. In particular, the distance between the leading edge 330 of the rail 314 and threaded holes 340 are the same for large, medium and small orthotic blanks 308, as shown in FIG. 29. In this manner, the threaded holes 340 of the blanks 308 are always aligned to the threaded bolts 338 when the blanks 308 are loaded onto the machining platen 298.

In an aspect of the milling apparatus 284, as stated above, the pins 366 of the laminator 294 may frictionally engage the holes 368 of the cover layer 310. In particular, the underside surface of the heating block 324 may have a plurality of spring loaded pins 366. Distal tips of the pins 366 may extend below the gel 328, as shown in FIG. 25. The pins 366 may retract into the heating block 324 or into the gel 328 provided that sufficient upward force is applied to the pins 366. Also, the force of the spring may be greater than the frictional force between the pin 366 and the hole 368 of the cover layer 310. The holes 368 formed in the cover layer 310 may be sized and configured to frictionally engage the pins 366. The holes 368 may also be positioned to line up with the pins 366. As such, when the laminator 294 is traversed to the engaged position, as stated above, the pins 366 are pushed through the holes 368. The pins 366 are slightly larger compared to the holes 368 such that there is a friction fit between the pins 366 and holes 368. Any pins 366 which do not align with the holes 368 are retracted into the heating block 324 or gel 328. When the laminator 294 is traversed to the retracted position, the frictional forces between the pins 366 and the holes 368 lift the cover layer 310 off of the orthotic blanks 308a, b. Also, after the cover layer 310 is adhered to the orthotic blanks 308 after milling, the adhesive force is greater than the friction force between the pins 366 and the holes 368 such that the cover layer 310 is now transferred to the orthotic blank 308 for subsequent final cutting or milling.

The orthotic blanks 308 may be provided in a plurality of different sizes, as shown in FIG. 27A. Preferably, the orthotic blanks 308 are provided in three different sizes (i.e., small, medium and large) to fit small sized feet, medium sized feet and large sized feet. Each of the left and right orthotic blank 308a, b may be sized to be larger than an effective area 370 (see FIG. 26) of the orthotic blank 308. The excess material of the orthotic blank 308 outside of the effective area 370 provides support to the cover layer 310 such that the pins 366 do not merely bend the cover layer 310 downward but that the pins 366 may be pushed into the holes 368 of the cover layer 310 when the laminator 294 is traversed to the engaged position. When the orthotic blanks 308 are milled via the milling section, the holes 368 of the cover layer 310 may be milled off for being positioned outside of the effective area 270 of the orthotic blanks 308, as shown by the dashed lines 372 in FIG. 26.

FIG. 25A shows possible locations of the pins 366, and thus the holes 368 of the cover layer 310 for the small, medium and large sizes. In particular, the front two holes 368a (see FIG. 26) of the cover layer for the small, medium and large orthotic blanks may be located in the same position. As such, the two pins 366a (see FIG. 25A) may be sufficient to hold the frontal portion of the cover layers 310 sized for the small, medium and large orthotic blanks 308. The rearwardmost pins 366b (see FIG. 25A) may engage the rear two holes 368b (see FIG. 26) of the cover layer 310 for large orthotic blanks 308. The middle pins 366c (see FIG. 25A) may engage the rear two holes 368b (see FIG. 26) of the cover layer 310 for medium orthotic blanks. The front pins 366d (see FIG. 25A) may engage the rear two holes 368b (see FIG. 26) of the cover layer 310 for small orthotic blanks 308.

In an aspect of the milling apparatus 284, the rail 314 is received into the groove 322 of the upper gripper 302, grooves of the first and second upper rollers 374b,c and the groove 354 of the heating block 324 such that the orthotic blanks 308 are not skewed when being traversed into the laminator section 294. The rail 314 prevents the upper and lower grippers 302, 304 or the first and second upper rollers 374b, c from twisting the orthotic blanks 308 as the orthotic blanks 308 enter the laminator section 294. Typically, the upper and lower grippers 302, 304 and the first and second upper rollers 374b, c have minute differences in diameters and different coefficients of friction along the width of the grippers and rollers. As such, one side of the orthotic blanks 308 tends to enter the laminator section 294 faster than the other side. The orthotic blanks 308 enter the laminator section 294 in a skewed or rotated orientation. Fortunately, the grooves 322, 354 and the grooves of the first and second upper rollers 374b,c aligns the orthotic blanks 308 when the rails 314 enter the grooves 322, 354 and/or the grooves of the first and second upper rollers 374b,c such that the orthotic blanks 308 enter the laminator section 294 aligned to the laminator section 294/machining platform 298.

The display 14 may be in communication with the computer and may be operative to display a series of instructions transmitted by the computer to the display to guide the purchaser in operating the orthotic vending machine 10. The display 14 may also receive the pressure distribution information from the computer and display the pressure distribution information illustrating how the underside surfaces of the user's feet support the user's weight, as shown in FIG. 9. For example, an outline 146 of the person's feet may be displayed on the display 14. Areas of high pressure may be color coded in red, areas of low pressure may be color coded in yellow, and intermediate pressures may be color coded in varying shades of orange.

The computer may also have a communications port for providing a communications pathway 148 to a server 150, a financial institution 152, or a podiatrist 154, as shown in FIG. 1. The communications pathway 148 may be provided via the internet, local area network or wide area network system. The server 150 may have a database of inner surface contours of shoes from various shoe manufacturers. The server may download the inner surface contours of shoes to the vending machine computer as new model shoes are introduced by shoe manufacturers via the communications pathway 148.

The vending machine 10 may also be attached to a credit card or ATM reader 156 (see FIG. 1). The ATM reader 156 may transmit the purchaser's credit card or ATM card information to the financial institution 152 such that the user may purchase the customized orthotic 12 at the vending machine 10.

The vending machine 10 may gather initial health information about the purchaser's feet condition. If the computer decides that the purchaser may not be fitted with the customized orthotics 12 then the user may be placed in direct communication with the podiatrist 154 via the communications pathway 148. The user may verbally communicate with the podiatrist 154 via a speaker and microphone 158 (see FIG. 1) attached to the vending machine 10. Alternatively, the user may communicate with the podiatrist 154 in an online chat format with a keyboard attached to the vending machine 10. Alternatively the user may be referred to specialists that partake in our referral service.

Figure 10:
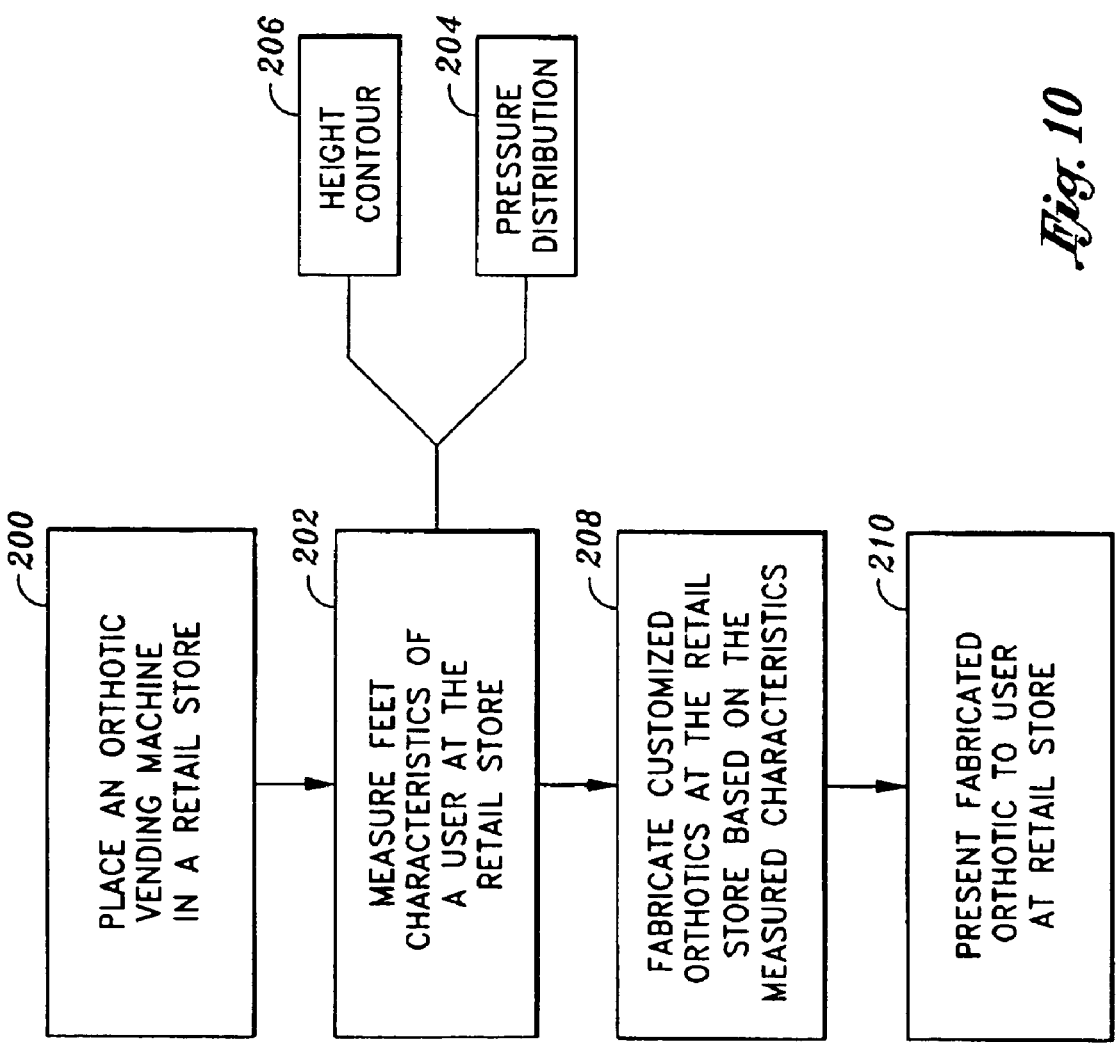
FIG. 10 is a flow chart of a method of producing orthotics with the vending machine.

In another aspect of the vending machine 10, a method of producing the customized orthotics 12 in a retail environment is provided, as shown in FIG. 10. In step 200, the orthotic vending machine 10 may be placed in a retail store. Preferably, the retail store is a shoe store. The display 14 of the vending machine 10 may display advertisements to inform potential shoppers of features and benefits of having customized orthotics 12. The platforms 22a, b may have indicia in the shape of feet silhouettes illustratively instructing the shopper to stand upon the platforms 22a, b with his/her feet aligned to the feet silhouette.

Once the shopper stands on the platforms 22a, b, the shopper may depress a start button at the bottom of the touch screen display 14. The display 14 may then ask the shopper a series of questions relating to the shopper's general information, medical history and his/her feet. The shopper may input the information via a keyboard on the touch screen display 14. By way of example and not limitation, the general information about the shopper may be sex, age, weight, and height. By way of example and not limitation, the medical history of the shopper may include whether the shopper is a diabetic, prior or current use of orthotics, known foot problems, etc. After the basic information and medical information is received by the computer, the display 14 may instruct the shopper to "not move your feet" and press "continue." After the "continue" button has been depressed, the vending machine 10 may measure various characteristics of the shopper's feet, as shown in step 202. In particular, the probes 28 may be vertically traversed until top surfaces 42 of the hex caps 34 or square caps 286 are in a common plane, and the pressure sensors 52 or the pressure sensor mat 288 may sense pressure distribution of the underside surfaces of the user's feet. The probes 28 may be traversed up and down to simulate the inner surface contours of shoes and to redistribute pressures on the underside surfaces of the shopper's feet. The pressure sensors 52 or the pressure sensor mat 288 and the computer may map pressure distribution of the underside surfaces of the shopper's feet, as shown in step 204. Also, the computer may track the heights of the top surfaces 42 of the hex caps 34 or square caps 286 to derive height contours of the shopper's feet, as shown in step 206. The computer may transmit the mapped pressure distribution to the display 14 showing high pressure with a red color, low pressure with a yellow color and intermediate pressures in shades of orange. The displayed pressure distribution may illustrate the outline 146 of the feet with pressure readings at each pressure sensor 52 location or via the pressure sensor mat 288. The shoe size of the person may be derived from the mapped pressure distribution and displayed to the user for the user's verification. The display 14 may then request the shopper to indicate any areas of current or intermittent foot soreness or discomfort. Thereafter, the computer may request that the shopper verify the information manually gathered from the shopper and derived from the mapped pressure distribution.

If the gathered and derived information indicates that the vending machine 10 may not be able to produce customized orthotics 12 for the shopper, then the computer may ask the shopper to discontinue use of the vending machine 10 and ask whether the shopper would like a referral to a podiatrist 154 in the local area. If the gathered and derived information indicate that the vending machine 10 may be able to produce the customized orthotics 12 for the shopper, then the display 14 requests the shopper to select the shoes to be used with the customized orthotics 12. By way of example and not limitation, the shopper may be asked about the shoe type (e.g., dress, athletic, boot, etc.), the shoe manufacturer (e.g., ALFANI, NIKE, PUMA, etc.) and shoe size. Once the shoes have been selected, the display 14 asks whether the shopper would like to feel how the shoes will feel without the customized orthotics 12. If the shopper selects "yes", then the computer retrieves the inner surface contours of the selected shoes and commands the probes 28 to move vertically to simulate the inner surface contours of the selected shoes.

The display 14 then asks the shopper whether they are satisfied with the feel of the shoes without corrective orthotics 12 and whether the shopper would like to purchase customized orthotics 12. The probes 28 are vertically traversed to simulate how the shoe will feel with the corrective orthotics 12 inserted into the shoes. The display 14 then asks the shopper whether he/she is satisfied with the feeling of the shoes with the customized orthotics 12. If the shoppers respond affirmatively, then the shopper may purchase the customized orthotics 12 directly via the vending machine 10 or with the cashier of the retail store. To purchase the customized orthotics 12 directly from the vending machine 10, the shopper may swipe his/her ATM or credit card into the reader 156. The ATM card or credit card information is transmitted to a financial institution 152 via the communications pathway 148 to debit the shopper's account. After purchase is confirmed, the customized orthotics 12 may be fabricated with the molding apparatus 18 or milling apparatus 284, as shown in step 208. The fabricated orthotics 12 may be presented to the shopper, as shown in step 210.

In an aspect of the measuring apparatus, the same has been described herein in relation to measuring the underside contour of a person's feet. However, it is also contemplated that the measuring apparatus may be employed to measure the surface contour of other objects. For example, the measuring apparatus may be employed to measure the surface contour of a fabricated part such as an airplane wing. For example, the hex caps or square caps may be replaced with a pointed cap such that when the probes are vertically traversed, the apex of the pointed cap contacts the surface to be measured. The surface to be measured may be placed on the platform and the probes adjusted until the apexes of the pointed caps contact the surface to be measured. The position of the apexes may be calculated, as discussed above, and transmitted to a computer for further processing.

The above description is given by way of example, and not limitation. Given the above disclosure, one skilled in the art could devise variations that are within the scope and spirit of the invention disclosed herein. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A method of providing orthotics to a person, the method comprising the steps of:
    a) providing an orthotic machine:
    b) measuring pressure distribution on underside surfaces of a person's feet with the orthotic machine;
    c) reconfiguring a platform of the orthotic machine until the pressure distribution on the underside surfaces of the person's feet meets with a diagnostic algorithm of the orthotic machine;
    d) measuring a height contour of the platform of the orthotic machine after the reconfiguring step;
    e) fabricating the orthotics with the machine based on the measured height contour of the platform;
    f) adjusting the height of the platform between first and second states, the first state being when the platform emulates an inner contour of a shoe and the second state being when the measured pressure distribution on the underside surfaces of the person's feet is optimal for permitting the person to virtually compare the shoe with and without the orthotics.

2. The method of claim 1 wherein the platform is reconfigured until the pressure distribution on the underside surfaces of the person's feet is equalized.

* * * * *